(12) United States Patent
Ingber et al.

(10) Patent No.: US 10,753,940 B2
(45) Date of Patent: Aug. 25, 2020

(54) ENHANCED ELECTROCHEMICAL DETECTION USING NANOPARTICLES AND PRECIPITATION

(71) Applicant: PRESIDENT AND FELLOWS OF HARVARD COLLEGE, Cambridge, MA (US)

(72) Inventors: Donald E. Ingber, Boston, MA (US); Olivier Y. F. Henry, Brookline, MA (US); Michael Super, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/749,976

(22) PCT Filed: Aug. 3, 2016

(86) PCT No.: PCT/US2016/045369
§ 371 (c)(1),
(2) Date: Feb. 2, 2018

(87) PCT Pub. No.: WO2017/024044
PCT Pub. Date: Feb. 9, 2017

(65) Prior Publication Data
US 2018/0217148 A1 Aug. 2, 2018

Related U.S. Application Data

(60) Provisional application No. 62/200,454, filed on Aug. 3, 2015.

(51) Int. Cl.
*G01N 33/58* (2006.01)
*G01F 1/64* (2006.01)
(Continued)

(52) U.S. Cl.
CPC .............. *G01N 33/581* (2013.01); *C12Q 1/68* (2013.01); *C12Q 1/6816* (2013.01); *G01F 1/64* (2013.01);
(Continued)

(58) Field of Classification Search
CPC .............. G01N 33/581; G01N 33/585; G01N 33/5438; C12Q 1/68; G01F 1/64; B82Y 30/00
See application file for complete search history.

(56) References Cited

U.S. PATENT DOCUMENTS

| | | | |
|---|---|---|---|
| 6,391,558 B1 * | 5/2002 | Henkens | C12Q 1/6825 435/6.11 |
| 2005/0003399 A1 | 1/2005 | Blackburn et al. | |

(Continued)

FOREIGN PATENT DOCUMENTS

WO  WO2013/012924  *  1/2013

OTHER PUBLICATIONS

Castillo et al., "Glutamate detection from nerve cells using a planar electrodes array integrated in a microtiter plate", Biosensors and Bioelectronics 20:2116-2119 (2005).
(Continued)

*Primary Examiner* — Melanie Brown
(74) *Attorney, Agent, or Firm* — Nixon Peabody LLP; David S. Resnick; Ravinderjit Braich

(57) ABSTRACT

The invention described herein relates generally to methods, sensors, devices and kits for electrochemical detection of a target analyte in a sample. In certain aspects, the methods, sensors, devices and kits described herein can be used to detect low concentrations of at least one target analyte using small sample volumes. In some embodiments, methods, sensors and kits for detecting a microbe, microbe fragment or released endotoxin in a test sample, including bodily fluids such as blood and tissues of a subject, food, water, and environmental surfaces, are also provided herein.

18 Claims, 15 Drawing Sheets

Specification includes a Sequence Listing.

(51) Int. Cl.
G01N 33/543 (2006.01)
C12Q 1/68 (2018.01)
C12Q 1/6816 (2018.01)
G01N 33/535 (2006.01)
B82Y 30/00 (2011.01)

(52) U.S. Cl.
CPC ....... *G01N 33/535* (2013.01); *G01N 33/5438* (2013.01); *B01J 2219/00653* (2013.01); *B82Y 30/00* (2013.01)

(56) References Cited

U.S. PATENT DOCUMENTS

| | | | |
|---|---|---|---|
| 2005/0136500 A1* | 6/2005 | Yang | G01N 33/52 435/14 |
| 2007/0231794 A1* | 10/2007 | Dill | C12Q 1/001 435/6.11 |
| 2012/0135530 A1 | 5/2012 | Bamdad et al. | |
| 2012/0157332 A1* | 6/2012 | Kumar | G01N 33/54386 506/9 |
| 2012/0283141 A1 | 11/2012 | Bieniarz et al. | |
| 2014/0073515 A1 | 3/2014 | Zeng et al. | |

OTHER PUBLICATIONS

Del Rio et al., "Electrochemical detection of Francisella tularensis genomic DNA using solid-phase recombinase polymerase amplification", Biosensors and Bioelectronics 54:674-678 (2014).

Hou et al., "Graphene oxide-labeled sandwich-type impedimetric immunoassay with sensitive enhancement based on enzymatic 4-chloro-1-naphthol oxidation", Biosensors and Bioelectronics 47:149-156 (2013).

La Belle et al., "Label-Free Impedimetric Detection of Glycan-Lectin Interactions", Analytical Chemistry 79(18):6959-6964 (2007).

Ley et al., "An electrochemical microtiter plate for parallel spectroelectrochemical measurements", Electrochimica Acta 89:98-105 (2013).

Lian et al., "Integrated microfluidic components on a printed wiring board platform", Sensors and Actuators B: Chemical 138:21-27 (2009).

Piermarini et al., "Electrochemical immunosensor array using a 96-well screen-printed microplate for aflatoxin B1 detection", Biosensors and Bioelectronics 22:1434-1440 (2007).

Steude et al., "An electrode array for electrochemical immuno-sensing using the example of impedimetric tenascin C detection", Lab on a Chip 11:2884-2892 (2011).

Tang et al., "Immunoassay with a Microtiter Plate Incorporated Multichannel Electrochemical Detection System", Analytical Chemistry 74(11):2617-2621 (2002).

Umek et al., "Electronic Detection of Nucleic Acids: A Versatile Platform for Molecular Diagnostics", Journal of Molecular Diagnostics 3(2):74-84 (2001).

Wan et al., "Development of electrochemical immunosensors towards point of care diagnostics", Biosensors and Bioelectronics 47:1-11 (2013).

Wang et al., "QCM Immunoassay for Phosphorylated Acetylcholinesterase as a Biomarker for Organophosphate Exposures Based on Selective Zirconia Adsorption and Enzyme-Catalytic Precipitation", Biosensors and Bioelectronics 24(8):2377 (2009). (15 pages).

Sanchez et al., "Multiplex PCB-based electrochemical detection of cancer biomarkers using MLPA-barcode approach", Biosensors and Bioelectronics, 82, 224-232, (2016).

\* cited by examiner

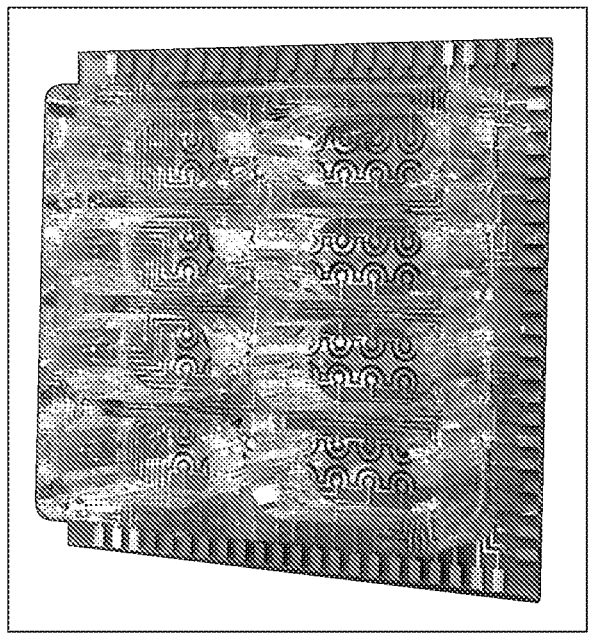
FIG. 4A Open cell
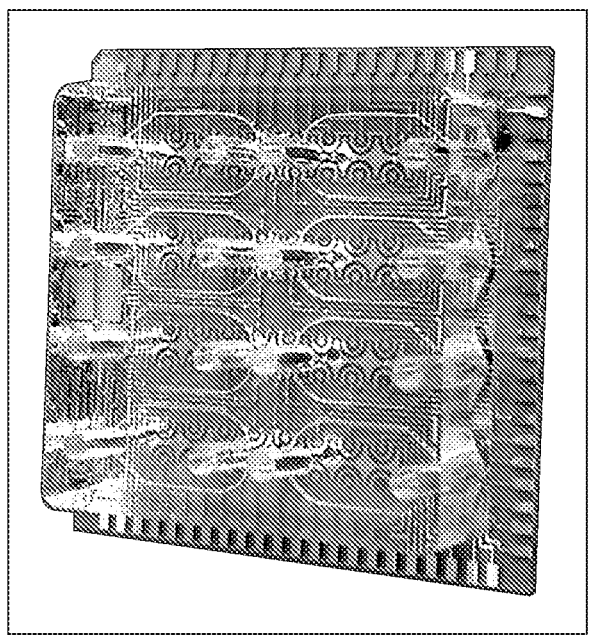
FIG. 4B Flow cell

SEQUENCE LISTING

```
<160> NUMBER OF SEQ ID NOS: 8

<210> SEQ ID NO 1
<211> LENGTH: 248
<212> TYPE: PRT
<213> ORGANISM: Unknown
<220> FEATURE:
<223> OTHER INFORMATION: Description of Unknown:
      Mannan-binding lectin

<400> SEQUENCE: 1

Met Ser Leu Phe Pro Ser Leu Pro Leu Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
        35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220
```

```
Leu Leu Lys Asn Gly Gln Trp Asn Asp Val Pro Cys Ser Thr Ser His
225                 230                 235                 240

Leu Ala Val Cys Glu Phe Pro Ile
                245
```

```
<210> SEQ ID NO 2
<211> LENGTH: 228
<212> TYPE: PRT
<213> ORGANISM: Unknown
<220> FEATURE:
<223> OTHER INFORMATION: Description of Unknown:
      Mannan-binding lectin

<400> SEQUENCE: 2
```

```
Glu Thr Val Thr Cys Glu Asp Ala Gln Lys Thr Cys Pro Ala Val Ile
1               5                   10                  15

Ala Cys Ser Ser Pro Gly Ile Asn Gly Phe Pro Gly Lys Asp Gly Arg
            20                  25                  30

Asp Gly Thr Lys Gly Glu Lys Gly Glu Pro Gly Gln Gly Leu Arg Gly
        35                  40                  45

Leu Gln Gly Pro Pro Gly Lys Leu Gly Pro Pro Gly Asn Pro Gly Pro
    50                  55                  60

Ser Gly Ser Pro Gly Pro Lys Gly Gln Lys Gly Asp Pro Gly Lys Ser
65                  70                  75                  80

Pro Asp Gly Asp Ser Ser Leu Ala Ala Ser Glu Arg Lys Ala Leu Gln
                85                  90                  95

Thr Glu Met Ala Arg Ile Lys Lys Trp Leu Thr Phe Ser Leu Gly Lys
            100                 105                 110

Gln Val Gly Asn Lys Phe Phe Leu Thr Asn Gly Glu Ile Met Thr Phe
        115                 120                 125

Glu Lys Val Lys Ala Leu Cys Val Lys Phe Gln Ala Ser Val Ala Thr
    130                 135                 140

Pro Arg Asn Ala Ala Glu Asn Gly Ala Ile Gln Asn Leu Ile Lys Glu
145                 150                 155                 160

Glu Ala Phe Leu Gly Ile Thr Asp Glu Lys Thr Glu Gly Gln Phe Val
                165                 170                 175

Asp Leu Thr Gly Asn Arg Leu Thr Tyr Thr Asn Trp Asn Glu Gly Glu
            180                 185                 190

Pro Asn Asn Ala Gly Ser Asp Glu Asp Cys Val Leu Leu Leu Lys Asn
        195                 200                 205

Gly Gln Trp Asn Asp Val Pro Cys Ser Thr Ser His Leu Ala Val Cys
    210                 215                 220

Glu Phe Pro Ile
225
```

```
<210> SEQ ID NO 3
<211> LENGTH: 141
<212> TYPE: PRT
<213> ORGANISM: Unknown
<220> FEATURE:
<223> OTHER INFORMATION: Description of Unknown:
      Mannan-binding lectin

<400> SEQUENCE: 3
```

```
Ala Ala Ser Glu Arg Lys Ala Leu Gln Thr Glu Met Ala Arg Ile Lys
1               5                   10                  15

Lys Trp Leu Thr Phe Ser Leu Gly Lys Gln Val Gly Asn Lys Phe Phe
            20                  25                  30
```

```
Leu Thr Asn Gly Glu Ile Met Thr Phe Glu Lys Val Lys Ala Leu Cys
            35                  40                  45

Val Lys Phe Gln Ala Ser Val Ala Thr Pro Arg Asn Ala Ala Glu Asn
 50                  55                  60

Gly Ala Ile Gln Asn Leu Ile Lys Glu Glu Ala Phe Leu Gly Ile Thr
 65                  70                  75                  80

Asp Glu Lys Thr Glu Gly Gln Phe Val Asp Leu Thr Gly Asn Arg Leu
                85                  90                  95

Thr Tyr Thr Asn Trp Asn Glu Gly Glu Pro Asn Asn Ala Gly Ser Asp
            100                 105                 110

Glu Asp Cys Val Leu Leu Leu Lys Asn Gly Gln Trp Asn Asp Val Pro
        115                 120                 125

Cys Ser Thr Ser His Leu Ala Val Cys Glu Phe Pro Ile
    130                 135                 140

<210> SEQ ID NO 4
<211> LENGTH: 115
<212> TYPE: PRT
<213> ORGANISM: Unknown
<220> FEATURE:
<223> OTHER INFORMATION: Description of Unknown:
      Mannan-binding lectin

<400> SEQUENCE: 4

Val Gly Asn Lys Phe Phe Leu Thr Asn Gly Glu Ile Met Thr Phe Glu
 1               5                  10                  15

Lys Val Lys Ala Leu Cys Val Lys Phe Gln Ala Ser Val Ala Thr Pro
            20                  25                  30

Arg Asn Ala Ala Glu Asn Gly Ala Ile Gln Asn Leu Ile Lys Glu Glu
                35                  40                  45

Ala Phe Leu Gly Ile Thr Asp Glu Lys Thr Glu Gly Gln Phe Val Asp
 50                  55                  60

Leu Thr Gly Asn Arg Leu Thr Tyr Thr Asn Trp Asn Glu Gly Glu Pro
 65                  70                  75                  80

Asn Asn Ala Gly Ser Asp Glu Asp Cys Val Leu Leu Leu Lys Asn Gly
                85                  90                  95

Gln Trp Asn Asp Val Pro Cys Ser Thr Ser His Leu Ala Val Cys Glu
            100                 105                 110

Phe Pro Ile
        115

<210> SEQ ID NO 5
<211> LENGTH: 148
<212> TYPE: PRT
<213> ORGANISM: Unknown
<220> FEATURE:
<223> OTHER INFORMATION: Description of Unknown:
      Mannan-binding lectin

<400> SEQUENCE: 5

Pro Asp Gly Asp Ser Ser Leu Ala Ala Ser Glu Arg Lys Ala Leu Gln
 1               5                  10                  15

Thr Glu Met Ala Arg Ile Lys Lys Trp Leu Thr Phe Ser Leu Gly Lys
            20                  25                  30

Gln Val Gly Asn Lys Phe Phe Leu Thr Asn Gly Glu Ile Met Thr Phe
                35                  40                  45

Glu Lys Val Lys Ala Leu Cys Val Lys Phe Gln Ala Ser Val Ala Thr
 50                  55                  60
```

Pro Arg Asn Ala Ala Glu Asn Gly Ala Ile Gln Asn Leu Ile Lys Glu
65                  70                  75                  80

Glu Ala Phe Leu Gly Ile Thr Asp Glu Lys Thr Glu Gly Gln Phe Val
                85                  90                  95

Asp Leu Thr Gly Asn Arg Leu Thr Tyr Thr Asn Trp Asn Glu Gly Glu
            100                 105                 110

Pro Asn Asn Ala Gly Ser Asp Glu Asp Cys Val Leu Leu Leu Lys Asn
        115                 120                 125

Gly Gln Trp Asn Asp Val Pro Cys Ser Thr Ser His Leu Ala Val Cys
    130                 135                 140

Glu Phe Pro Ile
145

<210> SEQ ID NO 6
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Pro Asp Gly Asp Ser Ser Leu Ala
225                 230                 235                 240

Ala Ser Glu Arg Lys Ala Leu Gln Thr Glu Met Ala Arg Ile Lys Lys
                245                 250                 255

Trp Leu Thr Phe Ser Leu Gly Lys Gln Val Gly Asn Lys Phe Phe Leu
            260                 265                 270

```
Thr Asn Gly Glu Ile Met Thr Phe Glu Lys Val Lys Ala Leu Cys Val
        275                 280                 285

Lys Phe Gln Ala Ser Val Ala Thr Pro Arg Asn Ala Ala Glu Asn Gly
        290                 295                 300

Ala Ile Gln Asn Leu Ile Lys Glu Ala Phe Leu Gly Ile Thr Asp
305                 310                 315                 320

Glu Lys Thr Glu Gly Gln Phe Val Asp Leu Thr Gly Asn Arg Leu Thr
                325                 330                 335

Tyr Thr Asn Trp Asn Glu Gly Glu Pro Asn Asn Ala Gly Ser Asp Glu
            340                 345                 350

Asp Cys Val Leu Leu Lys Asn Gly Gln Trp Asn Asp Val Pro Cys
        355                 360                 365

Ser Thr Ser His Leu Ala Val Cys Glu Phe Pro Ile
        370                 375                 380

<210> SEQ ID NO 7
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Pro Asp Gly Asp Ser
225                 230                 235                 240

Ser Leu Ala Ala Ser Glu Arg Lys Ala Leu Gln Thr Glu Met Ala Arg
```

```
                245                 250                 255
Ile Lys Lys Trp Leu Thr Phe Ser Leu Gly Lys Gln Val Gly Asn Lys
            260                 265                 270

Phe Phe Leu Thr Asn Gly Glu Ile Met Thr Phe Glu Lys Val Lys Ala
            275                 280                 285

Leu Cys Val Lys Phe Gln Ala Ser Val Ala Thr Pro Arg Asn Ala Ala
            290                 295                 300

Glu Asn Gly Ala Ile Gln Asn Leu Ile Lys Glu Glu Ala Phe Leu Gly
305                 310                 315                 320

Ile Thr Asp Glu Lys Thr Glu Gly Gln Phe Val Asp Leu Thr Gly Asn
                325                 330                 335

Arg Leu Thr Tyr Thr Asn Trp Asn Glu Gly Glu Pro Asn Asn Ala Gly
                340                 345                 350

Ser Asp Glu Asp Cys Val Leu Leu Leu Lys Asn Gly Gln Trp Asn Asp
            355                 360                 365

Val Pro Cys Ser Thr Ser His Leu Ala Val Cys Glu Phe Pro Ile
            370                 375                 380

<210> SEQ ID NO 8
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220
```

-continued

```
Ser Leu Ser Leu Ser Pro Gly Ala Thr Ser Lys Gln Val Gly Asn Lys
225                 230                 235                 240

Phe Phe Leu Thr Asn Gly Glu Ile Met Thr Phe Glu Lys Val Lys Ala
            245                 250                 255

Leu Cys Val Lys Phe Gln Ala Ser Val Ala Thr Pro Arg Asn Ala Ala
            260                 265                 270

Glu Asn Gly Ala Ile Gln Asn Leu Ile Lys Glu Glu Ala Phe Leu Gly
        275                 280                 285

Ile Thr Asp Glu Lys Thr Glu Gly Gln Phe Val Asp Leu Thr Gly Asn
    290                 295                 300

Arg Leu Thr Tyr Thr Asn Trp Asn Glu Gly Glu Pro Asn Asn Ala Gly
305                 310                 315                 320

Ser Asp Glu Asp Cys Val Leu Leu Leu Lys Asn Gly Gln Trp Asn Asp
            325                 330                 335

Val Pro Cys Ser Thr Ser His Leu Ala Val Cys Glu Phe Pro Ile
            340                 345                 350
```

ENHANCED ELECTROCHEMICAL DETECTION USING NANOPARTICLES AND PRECIPITATION

CROSS REFERENCE TO RELATED APPLICATIONS

This application is a 371 National Phase Entry of International Patent Application No. PCT/US2016/045369 filed on Aug. 3, 2016 which claims benefit under 35 U.S.C. § 119(e) of the U.S. Provisional Application No. 62/200,454, filed Aug. 3, 2015 contents of which are incorporated herein by reference in their entirety.

GOVERNMENT SUPPORT

This invention was made with government support under Contract No. N66001-11-1-4180 awarded by the Space and Warfare Systems Command. The government has certain rights in the invention.

SEQUENCE LISTING

The instant application contains a Sequence Listing which has been submitted electronically in ASCII format and is hereby incorporated by reference in its entirety. Said ASCII copy, created on Jul. 29, 2016, is named 002806-084981-PCT_SL.txt and is 18,380 bytes in size.

TECHNICAL FIELD

The invention described herein relates generally to methods, sensors, devices and kits for electrochemical detection of a target analyte in a sample. In certain aspects, the methods, sensors, devices and kits described herein can be used to detect low concentrations of at least one target analyte using small sample volumes. In some embodiments, methods, sensors and kits for detecting a microbe, microbe fragment or released endotoxin in a test sample, including bodily fluids such as blood and tissues of a subject, food, water, and environmental surfaces, are also provided herein.

BACKGROUND

Current immunoassays such as enzyme linked immunosorbant assay (ELISA) performed in 96-well microtiter plate requires a minimum sample volume of 50 µL per well, i.e. 150 µL to perform the test in triplicate. In addition, the sample can only be tested for a single chemical or biochemical (e.g. protein, toxin, drug) in a given well. Commercial alternatives for the multiplexed detection of several biochemicals exist (e.g. Luminex (Life Technologies Corp.)) but are expensive, require extensive preparative steps and relatively large sample volumes. There is a need for more sensitive, miniaturised and faster multiplexed assays. In addition, the immunoassay format limits the spatial resolution over the enzymatic reaction, i.e. the entire well turns "positive". This makes difficult to address multiples analytes in a single sample. Sample volumes become problematic. Colorimetric microarray-in-wells have been developed but lack sensitivity, and require expensive instrumentation (e.g. optics, laser scanner, etc.).

Electrochemical sensor platforms have been previously reported [see e.g., Wan, Y., et al., *Development of electrochemical immunosensors towards point of care diagnostics*. Biosensors and Bioelectronics, 2013. 47(0): p. 1-11. Ley, C., et al., *An electrochemical microtiter plate for parallel spectroelectrochemical measurements*. Electrochimica Acta, 2013. 89(0): p. 98-105. Piermarini, S., et al., *Electrochemical immunosensor array using a 96-well screen-printed microplate for aflatoxin B1 detection*. Biosensors and Bioelectronics, 2007. 22(7): p. 1434-1440. Tang, T.-C., A. Deng, and H.-J. Huang, *Immunoassay with a Microtiter Plate Incorporated Multichannel Electrochemical Detection System*. Analytical Chemistry, 2002. 74(11): p. 2617-2621. Castillo, J., et al., *Glutamate detection from nerve cells using a planar electrodes array integrated in a microtiter plate*. Biosensors and Bioelectronics, 2005. 20(10): p. 2116-2119]. However, the existing electrochemical sensor platforms are singleplex, i.e. only one electrode per well, dedicated to the measurement of only one biochemical. The disposable electrode arrays are comparatively costly, as high-end electrodes arrays are ideally photolithographically microfabricated under clean room environment. In addition, diffusion of the oxidized substrate to neighboring electrodes can cause severe background current and lead to a number of errors in the interpretation of the results.

The sensitive detection of pathogens/pathogen fragments/endotoxins with a sensitivity equal to 1 CFU/mL (CFU=colony forming unit) is a challenging task. Most systems rely on large equipment and tedious analytical procedures. The ability to detect pathogens at those levels would enable the development of a companion diagnostic able to provide a rapid answer on the level of contamination present in a sample. Accordingly, there is a need to develop a method or approach that is sensitive enough to detect low concentrations of analyte and is also versatile enough to detect multiple analytes simultaneously.

SUMMARY OF THR INVENTION

Certain aspects of the present invention described herein are, at least in part, directed to a method for detecting a target analyte in a sample, comprising:
(a) introducing a sample comprising a target analyte into an electrochemical sensor comprising a fluid-contact surface and an analyte-specific electrode immobilized on at least a portion of the fluid-contact surface, wherein the analyte-specific electrode is functionalized with a capture probe for specific binding with the target analyte;
(b) allowing the target analyte to bind with the capture probe on the analyte-specific electrode, thereby forming a complex comprising the target analyte and the capture probe on a surface of the analyte-specific electrode;
(c) labeling the complex with a label probe, wherein the label probe binds specifically with the target analyte and the label probe is conjugated with at least one reporter enzyme;
(d) introducing an electroactive mediator precipitating composition into the electrochemical sensor, wherein a reaction of the electroactive mediator precipitating composition with the at least one reporter enzyme conjugated with the label probe forms an electroactive precipitate locally adsorbed at the surface of the analyte-specific electrode;
(e) applying a voltage to the electrochemical sensor, wherein the voltage corresponds to the standard redox potential of the electroactive precipitate; and
(f) measuring a current generated from the analyte-specific electrode of the electrochemical sensor to detect the target analyte;
wherein the target analyte is not a nucleic acid.

In some embodiments, the method further comprises prior to step (a):
i. mixing a sample comprising the target analyte with a plurality of nanoparticles, wherein at least one nanoparticle of said plurality of nanoparticles is functionalized with a capture probe for specific binding with the target analyte; and
ii. allowing the target analyte to bind with the capture probe on said at least one nanoparticle.

In some embodiments, the electrochemical sensor comprises a plurality of analyte-specific electrodes immobilized on at least a portion of the fluid-contact surface, wherein each analyte-specific electrode in said plurality of analyte-specific electrodes is functionalized with a capture probe for specific binding with a specific target analyte. In some embodiments, at least two of the analyte-specific electrodes are adapted to detect different target analytes. In some embodiments, at least two different target analytes in the sample are detected.

In some embodiments, the target analyte is selected from the group consisting of a protein, a peptide, a polypeptide, a peptidomimetic, an antibody, an antibody fragment, an amino acid, a peptide aptamer, a peptidoglycan, a cell, microbial matter, a carbohydrate, an antigen, a lipid, a steroid, a hormone, a lipopolysaccharide, an endotoxin, a drug, a lipid-binding molecule, a cofactor, a small molecule, a toxin, and any combination thereof. In some embodiments, the protein is a glycoprotein. Exemplary microbial matter include, but are not limited to, bacteria, viruses, protozoa, fungi, yeast, microbes, parasites, any fragments thereof, and any combination thereof. Exemplary carbohydrates include, but are not limited to, mannose, mannan, N-acetyl glucosamine, fucose, a monosaccharide, a disaccharide, a trisaccharide, a polysaccharide, and any combination thereof.

In some embodiments comprising a nanoparticle, the nanoparticle may be a magnetic nanoparticle, a gold nanoparticle, a silver nanoparticle, a semiconductor nanoparticle, or a polymeric nanoparticle. In some embodiments, at least two of the nanoparticles are functionalized with capture probes for specific binding with at least two different target analytes.

Some embodiments of the method further comprise, prior to the step of applying the voltage to the electrochemical sensor, washing the electrochemical sensor to remove any electroactive mediator precipitating composition or electroactive precipitate that is not adsorbed at the analyte-specific electrode surface.

In some embodiments, the electrochemical sensor comprises one or more microfluidic flow cells. In some embodiments, the electrochemical sensor comprises one or more open wells. Some embodiments comprise both one or more microfluidic flow cells and one or more open wells.

In some embodiments, the analyte-specific electrode is a planar or 3-dimensional electrode. In some embodiments, the analyte-specific electrode comprises gold, silver, copper, platinum, aluminum, stainless steel, tungsten, indium tin oxide, titanium, lead, nickel, palladium, silicon, polyimide, parylene, benzocyclobutene, carbon, graphite, or any combination thereof. In some embodiments, the fluid-contact surface further comprises a counter electrode, a reference electrode, a positive control electrode, a negative control electrode, or any combination thereof immobilized thereon.

In some embodiments, the voltage applied to the electrochemical sensor corresponds to an electrochemical oxidation or reduction potential, or combination thereof, of the electroactive mediator in a fully or partially oxidized state. In some embodiments, the generated current corresponds to a reduction or oxidation current derived from reduction or oxidation of the fully or partially oxidized electroactive mediator. An exemplary voltage window includes, but is not limited to, about $-0.2V$ as reduction potential to $+0.2V$ as oxidation potential versus a reference electrode.

In some embodiments, the fluid-contact surface is a non-electrically conductive surface. Exemplary non-electrically conductive surfaces include, but are not limited to, plastic, poly(carbonate) (PC), poly(methyl methacrylate) (PMMA), cyclic olefin polymers (COP), cyclic olefin copolymers (COC), silicon nitride, parylene, kapton, styrene-ethylene-butylene-styrene (SEBS), poly-dimethysiloxane (PDMS), polyimide, silicon dioxide, and any combination thereof.

In some embodiments, the capture probe and the label probe are independently selected from the group consisting of an antibody, an antibody fragment, a carbohydrate-binding protein, a peptide, a polypeptide, an aptamer, a cell-binding molecule, a lipid-binding molecule, and any combination thereof. In some embodiments, the target analyte comprises a microbe, and the capture probe and label probe comprise a carbohydrate binding protein, wherein the carbohydrate binding protein comprises a carbohydrate recognition domain of mannan-binding lectin (MBL). In some embodiments, the carbohydrate recognition domain of MBL is conjugated to an Fc portion of an immunoglobin.

In some embodiments, at least one reporter enzyme is conjugated to the label probe before the label probe binds to the target analyte complex. In other embodiments, at least one reporter enzyme is conjugated to the label probe after the label probe binds to the target analyte complex. In some embodiments, the label probe is functionalized with biotin and said at least one reporter enzyme is conjugated to streptavidin. In some embodiments, the label probe first binds to the target analyte complex, and then the streptavidin conjugated to said at least one reporter enzyme binds to the biotin functionalized label probe.

In some embodiments, at least one reporter enzyme comprises horseradish peroxidase (HRP), alkaline phosphatase (AP), glucose oxidase (GOx), tyrosinase, urease, a DNAzyme, an aptazyme, or any combination thereof. In some embodiments, at least one reporter enzyme comprises HRP.

In some embodiments, the electroactive mediator precipitating composition comprises a reporter enzyme substrate and an electroactive mediator. Exemplary reporter enzyme substrates include, but are not limited to, hydrogen peroxide, carbamide peroxide, nucleotides, oligonucleotides, RNA, DNA, phosphorylated peptides, phosphorylated proteins, phosphorylated small molecules, glucose, phenols, tyrosine, dopamine, catechol, urea, and any combination thereof. In some embodiments, the reporter enzyme substrate is hydrogen peroxide. Exemplary electroactive mediators include, but are not limited to, 3,3',5,5'-tetramethylbenzidine (TMB), o-phenylenediamine dihydrochloride (OPD), 2,2'-Azinobis [3-ethylbenzothiazoline-6-sulfonic acid] (ABTS), p-Nitrophenyl Phosphate (PNPP), 3,3'-diaminobenzidine (DAB), 4-chloro-1-naphthol (4-CN), 5-bromo-4-chloro-3-indolylphosphate (BCIP), nitro blue tetrazolium (NBT), methylene blue, hydroquinone, ferrocene derivatives, and any combination thereof. In some embodiments, the electroactive mediator is TMB. In some embodiments, the electroactive mediator precipitating composition further comprises a precipitating agent. Exemplary precipitating agents include, but are not limited to, a water-soluble polymer, a pyrrolidinone polymer, a polyaniline, a polypyrrole, a polythiophene, alginic acid, methyl vinyl ether/maleic anhydride copolymer, dextran sulfate, carrageenan, and any combination thereof. In some embodiments, the precipitating agent is a pyrrolidinone polymer.

Certain aspects of the present invention described herein are, at least in part, directed to a kit for electrochemical multiplex detection of a plurality of target analytes in a sample comprising:
(a) an electrochemical sensor comprising a fluid-contact surface and a plurality of analyte-specific electrodes immobilized on at least a portion of the fluid-contact surface, wherein the analyte-specific electrodes are each functionalized with a capture probe for binding a specific target analyte;
(b) a plurality of label probes, wherein each label probe is for binding a specific target analyte, and wherein each label probe is conjugated to at least one reporter enzyme or is functionalized to be conjugated to at least one reporter enzyme; and
(c) an electroactive mediator precipitating composition comprising a reporter enzyme substrate, an electroactive mediator and a precipitating agent, wherein a reaction of the reporter enzyme substrate and the electroactive mediator with the reporter enzyme forms an electroactive precipitate locally adsorbed at the surface of the analyte-specific electrodes;
wherein none of the target analytes are nucleic acids.

Some embodiments further comprise a plurality of nanoparticles, wherein at least one nanoparticle of said plurality of nanoparticles is functionalized with a capture probe for specific binding with a target analyte. Exemplary nanoparticles include, but are not limited to, a magnetic nanoparticle, a gold nanoparticle, a silver nanoparticle, a semiconductor nanoparticle, or a polymeric nanoparticle.

In some embodiments, the electrochemical sensor comprises one or more open wells. In some embodiments, the electrochemical sensor comprises one or more microfluidic flow cells. Some embodiments comprise both, one or more microfluidic flow cells and one or more open wells.

In some embodiments, the capture probe and the label probe are independently selected from the group consisting of an antibody, an antibody fragment, a carbohydrate-binding protein, a peptide, a polypeptide, an aptamer, a cell-binding molecule, a lipid-binding molecule, and any combination thereof. In some embodiments, the target analyte comprises a microbe, and the capture probe and label probe comprise a carbohydrate binding protein, wherein the carbohydrate binding protein comprises a carbohydrate recognition domain of mannan-binding lectin (MBL). In some embodiments, the carbohydrate recognition domain of MBL is conjugated to an Fc portion of an immunoglobin.

In some embodiments, the label probes are functionalized with biotin and the reporter enzymes are conjugated to streptavidin, so that the label probes first bind to specific target analytes, and then the streptavidin conjugated to the reporter enzymes binds to the biotin functionalized label probes. Exemplary reporter enzymes include, but are not limited to, horseradish peroxidase (HRP), alkaline phosphatase (AP), glucose oxidase (GOx), tyrosinase, urease, a DNAzyme, a aptazyme, or any combination thereof. In some embodiments, at least one reporter enzyme comprises HRP.

In some embodiments, the electroactive mediator precipitating composition comprises a reporter enzyme substrate and an electroactive mediator. Exemplary reporter enzyme substrates include, but are not limited to, hydrogen peroxide, carbamide peroxide, nucleotides, oligonucleotides, RNA, DNA, phosphorylated peptides, phosphorylated proteins, phosphorylated small molecules, glucose, phenols, tyrosine, dopamine, catechol, urea, and any combination thereof. In some embodiments, the reporter enzyme substrate is hydrogen peroxide. Exemplary electroactive mediators include, but are not limited to, 3,3',5,5'-tetramethylbenzidine (TMB), o-phenylenediamine dihydrochloride (OPD), 2,2'-Azinobis [3-ethylbenzothiazoline-6-sulfonic acid] (ABTS), p-Nitrophenyl Phosphate (PNPP), 3,3'-diaminobenzidine (DAB), 4-chloro-1-naphthol (4-CN), 5-bromo-4-chloro-3-indolyl-phosphate (BCIP), nitro blue tetrazolium (NBT), methylene blue, hydroquinone, ferrocene derivatives, and any combination thereof. In some embodiments, the electroactive mediator is TMB. In some embodiments, the electroactive mediator precipitating composition further comprises a precipitating agent. Exemplary precipitating agents include, but are not limited to, a water-soluble polymer, a pyrrolidinone polymer, a polyaniline, a polypyrrole, a polythiophene, alginic acid, methyl vinyl ether/maleic anhydride copolymer, dextran sulfate, carrageenan, and any combination thereof. In some embodiments, the precipitating agent is a pyrrolidinone polymer.

Certain aspects of the present invention described herein are, at least in part, directed to an electrochemical sensor comprising:
(a) a fluid-contact surface and a plurality of analyte-specific electrodes immobilized on at least a portion of the fluid-contact surface, wherein the analyte-specific electrodes are each functionalized with a capture probe for binding a specific target analyte;
(b) a plurality of different nanoparticle-bound target analytes bound to the corresponding capture probes of the analyte-specific electrodes; and
(c) an electroactive precipitate locally adsorbed at the surfaces of at least some of the analyte-specific electrodes, wherein the electroactive precipitate is formed from a reaction of an electroactive mediator precipitating composition comprising a reporter enzyme substrate, an electroactive mediator and a precipitating agent, with a reporter enzyme coupled to the nanoparticle-bound target analytes;
wherein none of the target analytes are nucleic acids.

In some embodiments, the reporter enzyme is coupled to the nanoparticle-bound target analytes by specific binding of a label probe to the corresponding nanoparticle-bound target analytes, wherein the label probe is conjugated to the reporter enzyme.

BRIEF DESCRIPTION OF THE DRAWINGS

FIGS. 4A and 4B each show sensor chips according to embodiments of the invention and consisting of 64 sensing electrodes, individually addressable. Each sensing electrode is functionalized with a given capture probe (e.g. antibody, carbohydrate-binding protein, synthetic binding element, etc.). FIG. 4A shows an open well embodiment. FIG. 4B shows a flow cell embodiment. In these embodiments, the open wells or microfluidic cells are glued on top of the electrode array and used to confine samples and introduce various reagents and washing buffers to perform the assay steps. An antibody for IL-6 was immobilized using standard coupling chemistry.

DETAILED DESCRIPTION OF THE INVENTION

Figure 1:
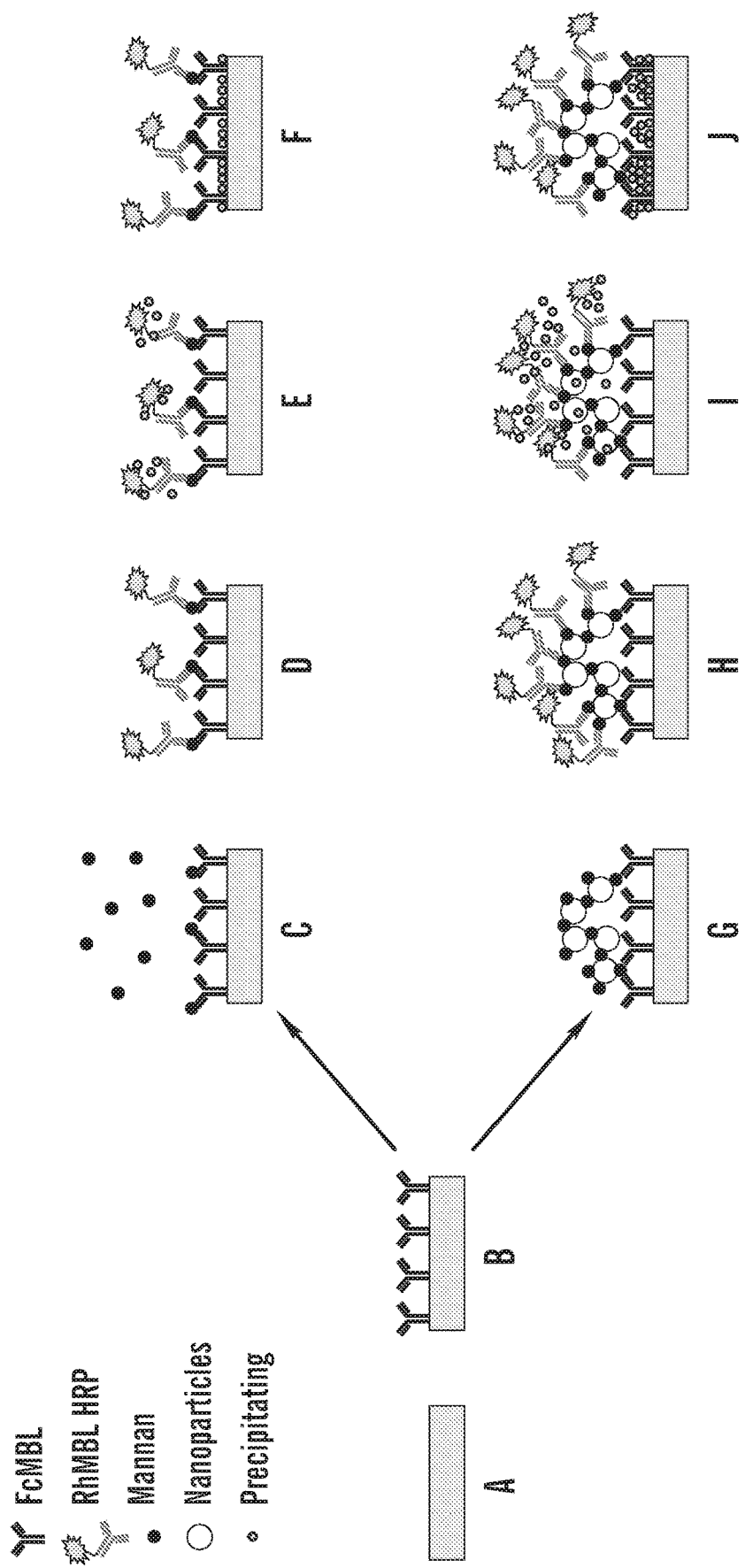
FIG. 1 is a schematic representation of an embodiment of a method for electrochemical detection of at least one target analyte in a sample.

Embodiments of various aspects described herein relate to methods, compositions, devices and kits for detecting at least one target analyte. Some embodiments provided herein relates to methods of detecting at least one target analyte, including, e.g., at least 2, 3, 4, 5, 6, 7, 8 target analytes or more. In some embodiments, a highly sensitive electrochemical detection method is disclosed for detecting and/or quantifying target analytes (e.g., proteins, carbohydrates, glycoproteins, cells, pathogens, pathogens fragments, released endotoxins, etc.). Advantageously, some embodiments of the disclosed method increase the sensitivity of detection by contacting a sample comprising a target analyte with nanoparticles coated with a capture probe specific for the target analyte prior to introducing the sample to an electrochemical sensor. In some embodiments, the combination of (i) localized electrochemical detection using an electroactive precipitate and (ii) sample pretreatment using nanoparticles coated with a capture probe, enables the highly sensitive detection of the target analyte and achieves multiplex target detection from a single sample, i.e., several target analytes can be detected in a single assay or well with minimal or no chemical cross-talk between electrodes due to the localized adsorption of electroactive precipitate.

In some embodiments, two or more target analytes can be detected simultaneously using an electrochemical sensor having one or more wells. As used herein, the term "detect" includes identifying the presence or absence of one or more target analytes, and can also include quantifying the amount and/or concentration of one or more target analytes in the sample. In some embodiments, each well of the electrochemical sensor comprises an inner bottom surface on which one or more analyte specific electrodes is immobilized. In some embodiments, the wells are open cells comprising open tops, enclosed sides and bottom, and one or more analyte-specific electrodes immobilized on the inner fluid-contact surface of the wells. In some embodiments, the electrochemical sensor comprises 1, 2, 3, 4, 5, 6, 8, 10, 12, 16, 24, 32, 48, 64, 96 or more open wells. FIG. 4A depicts an open cell embodiment having 8 open wells, and 8 electrodes in each well. Another embodiment is in the form of a 96-well microtiter plate. In some embodiments, the wells are microfluidic flow cells comprising an enclosed top, sides and bottom, wherein the top of each flow cell includes a fluid inlet and a fluid outlet, and comprising one or more analyte-specific electrodes immobilized on the inner fluid-contact surface of the wells. In some embodiments, the electrochemical sensor comprises 1, 2, 3, 4, 5, 6, 8, 10, 12, 16, 24, 32, 48, 64, 96 or more microfluidic flow cells. FIG. 4B depicts a flow cell embodiment having 8 enclosed wells, and 8 electrodes in each well. Another embodiment is in the form of a 96-well microtiter plate, wherein each well comprises an enclosed top having a fluid inlet and a fluid outlet. In some embodiments, the electrochemical sensor comprises both one or more open cells and one or more flow cells. Each well contains an array of analyte-specific electrodes (e.g., 32 gold electrodes) that can be individually modified with capture probes to bind the corresponding target analyte (e.g., pathogen, protein, carbohydrate, toxin, drug, etc.) present in the collected sample. In some embodiments, one sample is introduced into each well. In embodiments having two or more wells, portions of the same sample can be introduced into more than one well, or different samples can be introduced into different wells. Thus, in embodiments having multiple wells, multiple samples can be simultaneously assayed.

In some embodiments, the electrochemical sensor comprises (i) the analyte-specific electrodes on which the capture probes are immobilized; (ii) a contact pad, which connects the electrodes (e.g., analyte-specific electrodes, control electrodes, reference electrodes, etc.) to a measuring unit (i.e., readout instrumentation) (see for example the gold contact pads on the outer perimeter of the open cell and flow cell embodiments shown in FIGS. 4A-4B); and (iii) a conductive track that links (i) to (ii) (see for example the gold leads connecting the electrodes to the gold contact pads in the embodiments shown in FIGS. 4A-4B). In general, (iii) is not exposed to fluid samples, (iii) can be covered by a polymer layer (e.g., SU-8) or simply hidden from the fluid sample using microfluidics.

As used herein, an "electrode" is an electrical conductor used to make contact with a nonmetallic part of a circuit (i.e., it emits or collects electrons or electron "holes"). Electrodes can comprise any electrically conducting or semi-conducting material. Non-limiting examples include gold, silver, copper, platinum, aluminum, stainless steel, tungsten, indium tin oxide, titanium, lead, nickel, silicon, polyimide, parylene, benzocyclobutene, carbon, graphite, or any combination thereof. Preferably, electrodes comprise gold. The use of inexpensive gold-coated printed circuit board (PCB) substrates as electrochemical sensor platform has been reported [La Belle, J. T., et al., *Label-Free Impedimetric Detection of Glycan-Lectin Interactions*. Analytical Chemistry, 2007. 79(18): p. 6959-6964. Umek, R. M., et al., *Electronic Detection of Nucleic Acids: A Versatile Platform for Molecular Diagnostics*. The Journal of Molecular Diagnostics, 2001. 3(2): p. 74-84. Lian, K., et al., *Integrated microfluidic components on a printed wiring board platform*. Sensors and Actuators B: Chemical, 2009. 138(1): p. 21-27]. Metal patterning techniques, such as standard PCB technology, offer a number of versatile fabrication options such as (i) track size and spacing less than 100 µm; (ii) high purity electrolytic gold plating several microns thick suitable for electrochemistry and surface modification chemistries; (iii) ease of small scale prototyping in standard laboratory settings; and (iv) large scale mass manufacturing capabilities at a fraction of the cost of high-end microarrays. In some embodiments, electrodes as disclosed herein may be fabricated using PCB technology.

In some embodiments, the electrodes are mass fabricated onto non-electrically conductive surfaces such as plastic substrates using inexpensive standard technology such as printed circuit board (PCB) technology, roll-to-roll laser ablation or evaporation. Exemplary non-electrically conductive surfaces include plastic, poly(carbonate) (PC), poly (methyl methacrylate) (PMMA), cyclic olefin polymers (COP) or cyclic olefin copolymers (COC), SU-8, parylene, silicon nitride, kapton, styrene-ethylene-butylene-styrene (SEBS), poly-dimethysiloxane (PDMS), polyimide, silicon dioxide, and any combination thereof.

In some embodiments, the electrode is a planar or a 3-dimensional electrode. As used herein, a planar electrode electrically interacts with an electroactive species or mediator on a 2-dimensional surface. As used herein, a 3-dimensional electrode is an electrode displaying a very high surface area per unit volume, caused by no planarity. Without being bound by theory, this provides high turbulence at their interface with an electroactive species or mediator, enhancing the mass transfer process of the electroactive species towards the electrode surface. These characteristics strongly improve the electrochemical reaction rate.

Types of electrodes include analyte-specific electrodes, positive control electrodes, negative control electrodes, counter electrodes, reference electrodes, among other types. As used herein, "analyte-specific electrodes" are electrodes coated or otherwise functionalized with a capture probe for specific binding with a target analyte.

In some embodiments, the electrochemical sensor comprises 1, 2, 3, 4, 5, 6, 8, 10, 12, 16, 24, 32, 48 or more electrodes. In one embodiment, each well of the electrochemical sensor comprises 32 gold electrodes, which can enable the simultaneous detection of 1, 2, 3, 4, 5, 6, 7, or 8 different target analytes in triplicate, including positive and negative controls.

In some embodiments, the sensors consist of 300 µm diameter working electrodes that can be individually modified with receptor proteins (e.g. antibody, FcMBL) to capture their respective molecular targets. A reference electrode is used to control the potential or current applied at the working electrode and the resulting current is measured between the working and counter electrodes.

Generally, a single chip can be used to detect up to 64 proteins simultaneously. However, in some embodiments, measurements are realized in triplicate, including positive and negative controls. In some embodiments, negative controls consist of electrodes blocked with bovine serum albumin (BSA), for example, to limit non-specific adsorption. Negative controls allow monitoring background readings and eventually correct the protein sensor. In some embodiments, positive control electrodes are modified with BSA-biotin which can bind streptavidin-HRP, the label used in the last step of the assay in some embodiments. This can be used to confirm that all assay steps were realized successfully and that the chips are connected properly. The readings from positive controls can be used to normalize the protein sensors readings and compensate wells-to-wells variations.

In some embodiments, the target analyte can include a biological cell selected from the group consisting of living or dead cells (prokaryotic and eukaryotic, including mammalian), viruses, bacteria, fungi, yeast, protozoan, microbes, and parasites. The biological cell can be a normal cell or a diseased cell, e.g., a cancer cell. Mammalian cells include, without limitation; primate, human and a cell from any animal of interest, including without limitation; mouse, hamster, rabbit, dog, cat, domestic animals, such as equine, bovine, murine, ovine, canine, and feline. In some embodiments, the cells can be derived from a human subject. In other embodiments, the cells are derived from a domesticated animal, e.g., a dog or a cat. Exemplary mammalian cells include, but are not limited to, stem cells, cancer cells, progenitor cells, immune cells, blood cells, fetal cells, and any combinations thereof. The cells can be derived from a wide variety of tissue types without limitation such as, hematopoietic, neural, mesenchymal, cutaneous, mucosal, stromal, muscle, spleen, reticuloendothelial, epithelial, endothelial, hepatic, kidney, gastrointestinal, pulmonary, cardiovascular, T-cells, and fetus. Stem cells, embryonic stem (ES) cells, ES-derived cells, induced pluripotent stem cells, and stem cell progenitors are also included, including without limitation, hematopoietic, neural, stromal, muscle, cardiovascular, hepatic, pulmonary, and gastrointestinal stem cells. Yeast cells may also be used as cells in some embodiments described herein. In some embodiments, the cells can be ex vivo or cultured cells, e.g. in vitro. For example, for ex vivo cells, cells can be obtained from a subject, where the subject is healthy and/or affected with a disease. While cells can be obtained from a fluid sample, e.g., a blood sample, cells can also be obtained, as a non-limiting example, by biopsy or other surgical means known to those skilled in the art.

In some embodiments, the target analyte refers to a rare cell or a cellular component thereof. In some embodiments, the target analyte can refer to a rare cell or a cellular component thereof derived from a mammalian subject, including, without limitation, primate, human or any animal of interest such as mouse, hamster, rabbit, dog, cat, domestic animals, such as equine, bovine, murine, ovine, canine, and feline. In some embodiments, the rare cells can be derived from a human subject. In other embodiments, the rare cells can be derived from a domesticated animal or a pet such as a cat or a dog. As used herein, the term "rare cells" is defined, in some embodiments, as cells that are not normally present in a fluid sample, e.g., a biological fluid sample, but can be present as an indicator of an abnormal condition, such as infectious disease, chronic disease, injury, proliferative diseases, or pregnancy. In some embodiments, the term "rare cells" as used herein refers to cells that can be normally present in biological specimens, but are present with a frequency several orders of magnitude (e.g., at least about 100-fold, at least about 1000-fold, at least about 10000-fold) less than other cells typically present in a normal biological specimen. In some embodiments, rare cells are found infrequently in circulating blood, e.g., less than 100 cells (including less than 10 cells, less than 1 cell) per $10^8$ mononuclear cells in about 50 mL of peripheral blood. In some embodiments, a rare cell can be a normal cell or a diseased cell. Examples of rare cells include, but are not limited to, circulating tumor cells, progenitor cells, e.g., collected for bone marrow transplantation, blood vessel-forming progenitor cells, stem cells, circulating fetal cells, e.g., in maternal peripheral blood for prenatal diagnosis, virally-infected cells, cell subsets collected and manipulated for cell and gene therapy, and cell subpopulations purified for subsequent gene expression or proteomic analysis, other cells related to disease progression, and any combinations thereof.

As used herein, the term "a cellular component" in reference to circulating tumor cells, stem cells, fetal cells and/or microbes is intended to include any component of a cell that can be at least partially isolated from the cell, e.g., upon lysis of the cell. Cellular components can include, but are not limited to, organelles, such as nuclei, perinuclear compartments, nuclear membranes, mitochondria, chloroplasts, or cell membranes; polymers or molecular complexes, such as lipids, polysaccharides, proteins (membrane, trans-membrane, or cytosolic); nucleic acids, viral particles, or ribosomes; or other molecules, such as hormones, ions, and cofactors.

As used herein, the term "toxin" refers to a compound produced by an organism which causes or initiates the development of a noxious, poisonous or deleterious effect in a host presented with the toxin. Such deleterious conditions may include fever, nausea, diarrhea, weight loss, neurologic disorders, renal disorders, hemorrhage, and the like. Toxins include, but are not limited to, bacterial toxins, such as cholera toxin, heat-liable and heat-stable toxins of *E. coli*, toxins A and B of *Clostridium difficile*, aerolysins, and hemolysins; toxins produced by protozoa, such as *Giardia*; toxins produced by fungi. Molecular toxins can also include exotoxins, i.e., toxins secreted by an organism as an extracellular product, and enterotoxins, i.e., toxins present in the gut of an organism.

In some embodiments, the method described herein can be used to detect at least one of the following pathogens that causes diseases: *Bartonella henselae, Borrelia burgdorferi, Campylobacter jejuni, Campylobacter fetus, Chlamydia trachomatis, Chlamydia pneumoniae, Chylamydia psittaci, Simkania negevensis, Escherichia coli* (e.g., O157:H7 and K88), *Ehrlichia chafeensis, Clostridium botulinum, Clostridium perfringens, Clostridium tetani, Enterococcus faecalis, Haemophilus influenzae, Haemophilius ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum*, Human rhinovirus, Human coronavirus, Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, *Candida, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi*, among other viruses, bacteria, archaea, protozoa, and fungi).

In some embodiments, the method described herein can be used to detect bacteria present in a biofilm. For example, *Listeria monocytogenes* can form biofilms on a variety of materials used in food processing equipment and other food and non-food contact surfaces (Blackman, J Food Prot 1996; 59:827-31; Frank, J Food Prot 1990; 53:550-4; Krysinski, J Food Prot 1992; 55:246-51; Ronner, J Food Prot 1993; 56:750-8). Biofilms can be broadly defined as microbial cells attached to a surface, and which are embedded in a matrix of extracellular polymeric substances produced by the microorganisms. Biofilms are known to occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990: 195-231; Costerton et al., Annu Rev Microbiol 1995; 49:711-45).

In some embodiments, the method described herein can be used to detect a plant pathogen. Plant fungi have caused major epidemics with huge societal impacts. Examples of plant fungi include, but are not limited to, *Phytophthora infestans, Crinipellis perniciosa*, frosty pod (*Moniliophthora roreri*), oomycete *Phytophthora capsici, Mycosphaerella fijiensis, Fusarium Ganoderma* spp fungi and *Phytophthora*. An exemplary plant bacterium includes *Burkholderia cepacia*. Exemplary plant viruses include, but are not limited to, soybean mosaic virus, bean pod mottle virus, tobacco ring spot virus, barley yellow dwarf virus, wheat spindle streak virus, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus.

In yet other embodiments, the method described herein can be used to detect bioterror agents (e.g., B. *Anthracis*, and smallpox).

As used herein, the terms "capture probe" and "label probe" are used to describe an agent configured to detect and/or capture at least one target analyte as described herein. That is, the capture probe and label probe specifically bind to the target analyte to be detected. The capture probe can be present in any form, including but not limited to a target-binding molecule, and/or a target-binding substrate (e.g., a target-binding molecule conjugated to a solid substrate or a solid supporting structure such as an analyte specific electrode or a nanoparticle). As the present invention is directed to electrochemical detection of target analytes which are not nucleic acids (e.g., not DNA, not RNA, not oligonucleotides, etc.), the terms "capture probe" and "label probe" as used herein do not include nucleic acids. In some embodiments, the capture probe and/or label probe can comprise a target-binding molecule selected from the group consisting of peptides, polypeptides, proteins, peptidomimetics, antibodies, antibody fragments (e.g., antigen binding fragments of antibodies), carbohydrate-binding proteins (e.g., lectins, glycoproteins, glycoprotein-binding molecules), amino acids, carbohydrates (e.g., mono-, di-, tri- and poly-saccharides), lipids, steroids, hormones, lipid-binding molecules, cofactors, peptide aptamers, peptidoglycan, lipopolysaccharide, small molecules, endotoxins (e.g., bacterial lipopolysaccharides), and any combinations thereof.

In some embodiments, the capture probe and/or label probe comprises microbe-binding agents or molecules. In some embodiments, the target-binding molecules comprise microbe-binding molecules. Any molecule or material that can bind to a microbe can be employed as the microbe-binding molecule. Exemplary microbe-binding molecules (or microbe-binding molecules) include, but are not limited to, opsonins, lectins, antibodies and antigen binding fragments thereof, proteins, peptides, nucleic acids, carbohydrates, lipids, and any combinations thereof. The microbe-binding molecule can comprise at least one (e.g., one, two, three, four, five, six, seven, eight, nine, ten, eleven, twelve, thirteen, fourteen, fifteen, sixteen, seventeen, eighteen, nineteen, twenty or more) microbe surface-binding domain ("microbe binding domain"). The term "microbe surface-binding domain" as used herein refers to any molecules or a fragment thereof that can specifically bind to the surface of a microbe, e.g., any component present on a surface of a microbe.

Materials or substances which can serve as microbe-binding molecules include, for example, peptides, polypeptides, proteins, peptidomimetics, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof. The microbe-binding molecule can be covalently (e.g., cross-linked) or non-covalently linked to the substrate surface.

In some embodiments, the microbe surface-binding domain can comprise an opsonin or a fragment thereof. The term "opsonin" as used herein refers to naturally-occurring and synthetic molecules which are capable of binding to or attaching to the surface of a microbe or a pathogen, of acting as binding enhancers for a process of phagocytosis. Examples of opsonins which can be used in the engineered molecules described herein include, but are not limited to, vitronectin, fibronectin, complement components such as Clq (including any of its component polypeptide chains A, B and C), complement fragments such as C3d, C3b and C4b, mannose-binding protein, conglutinin, surfactant proteins A and D, C-reactive protein (CRP), alpha2-macroglobulin, and immunoglobulins, for example, the Fc portion of an immunoglobulin.

In some embodiments wherein the target analyte comprises a microbe or a fragment thereof, the capture probe and/or label probe can comprise a carbohydrate recognition domain derived from a carbohydrate-binding molecule. Examples of a carbohydrate-binding molecule include, but are not limited to, lectin, collectin, ficolin, mannose-binding lectin (MBL), maltose-binding protein, arabinose-binding protein, glucose-binding protein, *Galanthus nivalis* agglutinin, peanut lectin, lentil lectin, DC-SIGN, C-reactive protein, and any combinations thereof. In some embodiments, the label probe comprises a carbohydrate recognition domain and a reporter enzyme. In some embodiments, the capture probe or label probe is a fusion peptide comprising a carbohydrate recognition domain of a lectin. In a label probe, the fusion peptide is conjugated to a reporter enzyme. For example, the fusion peptide can be a FcMBL, which is a fusion peptide comprising mannan-binding lectin and a Fc portion of an immunoglobulin, and is described in the U.S. application Ser. No. 13/574,191 entitled "Engineered Opsonin for Pathogen Detection and Treatment" and U.S. application Ser. No. 14/233,553 entitled "Engineered Microbe-Targeting Molecules and Uses Thereof," both of which the patent applications are incorporated herein by reference. In some embodiments, a label probe can be a FcMBL conjugated to an enzyme label (e.g., but not limited to, horseradish peroxidase, alkaline phosphatase, a glucose oxidase, tyrosinase, urease, a DNAzyme, a aptazyme, etc.). Label probes such as FcMBL-HRP or FcMBL-AP described in U.S. application Ser. No. 14/233,553 entitled "Engineered Microbe-Targeting Molecules and Uses Thereof," incorporated by reference, can be also used herein.

In some embodiments, the microbe surface-binding domain comprises a carbohydrate recognition domain or a carbohydrate recognition portion thereof. As used herein, the term "carbohydrate recognition domain" refers to a region, at least a portion of which, can bind to carbohydrates on a surface of a microbe (e.g., a pathogen).

In some embodiments, the microbe surface-binding domain comprises a lectin or a carbohydrate recognition or binding fragment or portion thereof. The term "lectin" as used herein refers to any molecules including proteins, natural or genetically modified, that interact specifically with saccharides (i.e., carbohydrates). The term "lectin" as used herein can also refer to lectins derived from any species, including, but not limited to, plants, animals, insects and microorganisms, having a desired carbohydrate binding specificity. Examples of plant lectins include, but are not limited to, the Leguminosae lectin family, such as ConA, soybean agglutinin, peanut lectin, lentil lectin, and *Galanthus nivalis* agglutinin (GNA) from the *Galanthus* (snowdrop) plant. Other examples of plant lectins are the Gramineae and Solanaceae families of lectins. Examples of animal lectins include, but are not limited to, any known lectin of the major groups S-type lectins, C-type lectins, P-type lectins, and I-type lectins, and galectins. In some embodiments, the carbohydrate recognition domain can be derived from a C-type lectin, or a fragment thereof. C-type lectin can include any carbohydrate-binding protein that requires calcium for binding. In some embodiments, the C-type lectin can include, but are not limited to, collectin, DC-SIGN, and fragments thereof. Without wishing to be bound by theory, DC-SIGN can generally bind various microbes by recognizing high-mannose-containing glycoproteins on their envelopes and/or function as a receptor for several viruses such as HIV and Hepatitis C.

In some embodiments, the microbe-binding molecules or microbe-binding molecules can comprise a microbe-binding portion of the C-type lectins, including, e.g., but not limited to, soluble factors such as Collectins (e.g., MBL, surfactant protein A, surfactant protein D and Collectin 11), ficolins (e.g. L-Ficolin, Ficolin A), receptor based lectins (e.g., DC-SIGN, DC-SIGNR, SIGNR1, Macrophage Mannose Receptor 1, Dectin-1 and Dectin-2), lectins from the shrimp *Marsupenaeus japonicus* (e.g. Lectin A, Lectin B and Lectin C), or any combinations thereof.

In some embodiments, the microbe-binding molecules can comprise at least a portion of non-C-type lectins (e.g., but not limited to, Wheat Germ Agglutinin).

In some embodiments, the microbe-binding molecules can comprise at least a portion of lipopolysaccharide (LPS)-binding proteins and/or endotoxin binding proteins (e.g., but not limited to, CD14, MD2, lipopolysaccharide binding proteins (LBP), limulus anti-LPS factor (LAL-F), or any combinations thereof).

In some embodiments, the microbe-binding molecules can comprise at least a portion of peptidoglycan binding proteins (e.g., but not limited to, mammalian peptidoglycan recognition protein-1 (PGRP-1), PGRP-2, PGRP-3, PGRP-4, or any combinations thereof.

Collectins are soluble pattern recognition receptors (PRRs) belonging to the superfamily of collagen containing C-type lectins. Exemplary collectins include, without limitations, mannan-binding lectin (MBL) or mannose-binding protein, surfactant protein A (SP-A), surfactant protein D (SP-D), collectin liver 1 (CL-L1), collectin placenta 1 (CL-P1), conglutinin, collectin of 43 kDa (CL-43), collectin of 46 kDa (CL-46), and a fragment thereof.

In some embodiments, the microbe-surface binding domain comprises the full amino acid sequence of a carbohydrate-binding protein. In some embodiments, the microbe-surface binding domain comprises a sequence of a carbohydrate recognition domain of a carbohydrate-binding protein. Examples of carbohydrate-binding proteins include, but are not limited to, lectin, collectin, ficolin, mannose-binding lectin (MBL), maltose-binding protein, arabinose-binding protein, glucose-binding protein, *Galanthus nivalis* agglutinin, peanut lectin, lentil lectin, DC-SIGN, C-reactive protein (CRP), and any combinations thereof.

In some embodiments, the microbe surface-binding molecule comprises a mannose-binding lectin (MBL) or a carbohydrate binding fragment or portion thereof. Mannose-binding lectin, also called mannose binding protein (MBP), is a calcium-dependent serum protein that can play a role in the innate immune response by binding to carbohydrates on the surface of a wide range of microbes or pathogens (viruses, bacteria, fungi, protozoa) where it can activate the complement system. MBL can also serve as a direct opsonin and mediate binding and uptake of microbes or pathogens by tagging the surface of a microbe or pathogen to facilitate recognition and ingestion by phagocytes. MBL and an engineered form of MBL (FcMBL and Akt-FcMBL) are described in the International Application Publication Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), contents of both of which are incorporated herein by reference.

In some embodiments, the microbe surface-binding molecule comprises at least a portion of C-reactive protein that binds to a microbe or fragment thereof. Microbe-binding molecules comprising a portion of C-reactive protein described in U.S. Provisional App. No. 61/917,705 entitled "CRP Capture/Detection of Gram Positive Bacteria," the contents of which are incorporated herein by reference.

Without wishing to be bound by a theory, microbe binding molecules comprising lectins or modified versions thereof can act as broad-spectrum microbe binding molecules (e.g., pathogen binding molecules). Accordingly, antibiotic susceptibility method utilizing lectins (e.g., MBL and genetically engineered version of MBL (FcMBL and Akt-FcMBL)) as broad-spectrum microbe binding molecules (e.g., pathogen binding molecules) to capture and grow the microbes, can be carried out without identifying the microbe (e.g., pathogen), either for extraction or for antibiotic sensitivity testing.

In some embodiments, at least two microbe surface-binding domains (e.g. two, three, four, five, six, seven or more) microbe surface-binding domains, can be linked together to form a multimeric microbe surface-binding domain. In such embodiments, the distances between microbe surface-binding domains can be engineered to match with the distance between the binding sites on the target microbe surface. In some embodiments, the microbe surface-binding domain can be present in a form of a monomer, dimer, trimer, tetramer, pentamer, hexamer, or an entity comprising more than six sub-units.

A multimeric microbe surface-binding domain can have each of the individual microbe surface-binding domains to be identical. Alternatively, a multimeric microbe surface-binding domain can have at least one, at least two, or at least three microbe surface-binding domains different from the rest. In such embodiments, microbe surface-binding domains that share a common binding specificity for molecule on a microbe surface can be used. By way of example only, the fibrinogen-like domain of several lectins has a similar function to the CRD of C-type lectins including MBL, and function as pattern-recognition receptors to discriminate microbes or pathogens from self. One of such lectins comprising the fibrinogen-like domain is serum ficolins.

Serum ficolins have a common binding specificity for GlcNAc (N-acetyl-glucosamine), elastin or GalNAc (N-acetyl-galactosamine). The fibrinogen-like domain is responsible for the carbohydrate binding. In human serum, two types of ficolin, known as L-ficolin (also called P35, ficolin L, ficolin 2 or hucolin) and H-ficolin (also called Hakata antigen, ficolin 3 or thermolabile b2-macroglycoprotein), have been identified, and both of them have lectin activity. L-ficolin recognizes GlcNAc and H-ficolin recognizes GalNAc. Another ficolin known as M-ficolin (also called P3 5-related protein, ficolin 1 or ficolin A) is not considered to be a serum protein and is found in leucocytes and in the lungs. L-ficolin and H-ficolin activate the lectin-complement pathway in association with MASPs. M-Ficolin, L-ficolin and H-ficolin have calcium-independent lectin activity. Accordingly, in some embodiments, a microbe-binding molecule can comprise MBL and L-ficolin carbohydrate recognition domains, MBL and H-ficolin carbohydrate recognition domains, or a combination thereof.

Any art-recognized recombinant carbohydrate-binding proteins or carbohydrate recognition domains can also be used in the microbe-binding molecules. For example, recombinant mannose-binding lectins, e.g., but not limited to, the ones disclosed in the U.S. Pat. Nos. 5,270,199; 6,846,649; and U.S. Patent App. Publication No. US 2004/0229212, contents of all of which are incorporated herein by reference, can be used in constructing a microbe-binding molecule.

The microbe binding molecule can further comprise at least one (e.g., one, two, three, four, five, six, seven, eight, nine, ten, eleven, twelve, thirteen, fourteen, fifteen, sixteen, seventeen, eighteen, nineteen, twenty or more) substrate surface binding domain ("substrate binding domain") adapted for orienting the microbe binding domain away from the substrate surface. As used herein, the term "substrate-binding domain" refers to any molecule that facilitates the conjugation of the engineered molecules described herein to a solid substrate or a functionalized substrate. The microbe binding domain and the substrate binding domains can be linked by a linker. Similarly, the substrate binding domain and the substrate surface can be linked by a linker.

The substrate-binding domain can comprise at least one amino group that can non-covalently or covalently couple with functional groups on the surface of the substrate (e.g. an analyte-specific electrode, a nanoparticle, etc). For example, the primary amines of the amino acid residues (e.g., lysine or cysteine residues) at the N-terminus or in close proximity to the N-terminus of the microbe surface-binding domains can be used to couple with functional groups on the substrate surface.

In some embodiments, the substrate-binding domain can comprise at least one, at least two, at least three or more oligopeptides. The length of the oligonucleotide can vary from about 2 amino acid residues to about 10 amino acid residues, or about 2 amino acid residues to about 5 amino acid residues. Determination of an appropriate amino acid sequence of the oligonucleotide for binding with different substrates is well within one of skill in the art. For example, an oligopeptide comprising an amino acid sequence of Alanine-Lysine-Threonine (AKT), which provides a single biotinylation site for subsequent binding to streptavidin-coated substrate. Such single biotinylation site can also enable the microbe surface binding domain of a microbe binding molecule to orient away from the substrate, and thus become more accessible to microbes or pathogens. See, for example, Witus et al. (2010) J. Am. Chem. Soc. 132(47): 16812-17.

The microbe-binding molecules can contain sequences from the same species or from different species. For example, an interspecies hybrid microbe-binding molecule can contain a linker, e.g., a peptide linker, from a murine species, and a human sequence from a carbohydrate recognition domain protein, provided that they do not provide unacceptable levels of deleterious effects. The engineered microbe-binding molecules described herein can also include those that are made entirely from murine-derived sequences or fully human.

General methods of preparing such microbe-binding molecules are well known in the art (Ashkenazi, A. and S. M. Chamow (1997), "Immunoadhesins as research tools and therapeutic agents," Curr. Opin. Immunol. 9(2): 195-200, Chamow, S. M. and A. Ashkenazi (1996). "Immunoadhesins: principles and applications," Trends Biotechnol. 14(2):52-60). In one example, an engineered microbe-binding molecule can be made by cloning into an expression vector such as Fc-X vector as discussed in Lo et al. (1998) Protein Eng. 11:495 and PCT application no. PCT/US2011/021603, filed Jan. 19, 2011, contents of both of which is incorporated herein by reference.

In some embodiments, the microbe-binding molecule is a fusion protein or peptide comprising (a) a carbohydrate recognition domain derived from a carbohydrate binding protein, and (b) a linker as defined herein. In some embodiments, the fusion protein or peptide further comprise a substrate binding domain at one of its terminus (e.g., N-terminus), which permits a microbe-binding molecule to attach to a solid substrate such that the carbohydrate recognition domain points away from the solid substrate surface.

In one embodiment, the microbe-binding molecule comprises an MBL, a carbohydrate recognition domain of an MBL, or a genetically engineered version of MBL (FcMBL) as described in the International Application Publication Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), contents of both of which are incorporated herein by reference. Amino acid sequences for MBL and engineered MBL are:

(i) MBL full length (SEQ ID NO. 1):
MSLFPSLPLL LLSMVAASYS ETVTCEDAQK TCPAVIACSS

PGINGFPGKD GRDGTKGEKG EPGQGLRGLQ GPPGKLGPPG

NPGPSGSPGP KGQKGDPGKS PDGDSSLAAS ERKALQTEMA

RIKKWLTFSL GKQVGNKFFL TNGEIMTFEK VKALCVKFQA

SVATPRNAAE NGAIQNLIKE EAFLGITDEK TEGQFVDLTG

NRLTYTNWNE GEPNNAGSDE DCVLLLKNGQ WNDVPCSTSH

LAVCEFPI (ii) MBL without the signal sequence (SEQ ID NO. 2):
ETVTCEDAQK TCPAVIACSS PGINGFPGKD

GRDGTKGEKG EPGQGLRGLQ GPPGKLGPPG NPGPSGSPGP

KGQKGDPGKS PDGDSSLAAS ERKALQTEMA RIKKWLTFSL

```
GKQVGNKFFL TNGEIMTFEK VKALCVKFQA SVATPRNAAE

NGAIQNLIKE EAFLGITDEK TEGQFVDLTG NRLTYTNWNE

GEPNNAGSDE DCVLLLKNGQ WNDVPCSTSH LAVCEFPI (iii) Truncated MBL (SEQ ID NO. 3):
AASERKALQT EMARIKKWLT FSLGKQVGNK FFLTNGEIMT

FEKVKALCVK FQASVATPRN AAENGAIQNL IKEEAFLGIT

DEKTEGQFVD LTGNRLTYTN WNEGEPNNAG SDEDCVLLLK

NGQWNDVPCS TSHLAVCEFP I (iv) Carbohydrate recognition domain (CRD) of MBL
(SEQ ID NO. 4):
VGNKFFLTNG EIMTFEKVKA

LCVKFQASVA TPRNAAENGA IQNLIKEEAF LGITDEKTEG

QFVDLTGNRL TYTNWNEGEP NNAGSDEDCV LLLKNGQWND

VPCSTSHLAV CEFPI (v) Neck + Carbohydrate recognition domain of
MBL (SEQ ID NO. 5):
PDGDSSLAAS ERKALQTEMA RIKKWLTFSL GKQVGNKFFL

TNGEIMTFEK VKALCVKFQA SVATPRNAAE NGAIQNLIKE

EAFLGITDEK TEGQFVDLTG NRLTYTNWNE GEPNNAGSDE

DCVLLLKNGQ WNDVPCSTSH LAVCEFPI (vi) FcMBL.81 (SEQ ID NO. 6):
EPKSSDKTHT CPPCPAPELL GGPSVFLFPP KPKDTLMISR

TPEVTCVVVD V SHEDPEVKFNWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTPPVLDSDGSFF LYSKLTVDKS

RWQQGNVFSC SVMHEALHNH YTQKSLSLSP

GAPDGDSSLAASERKALQTE MARIKKWLTF SLGKQVGNKF

FLTNGEIMTF EKVKALCVKF QASVATPRNA AENGAIQNLI

KEEAFLGITD EKTEGQFVDL TGNRLTYTNW NEGEPNNAGS

DEDCVLLLKN GQWNDVPCST SHLAVCEFPI (vii) Akt-FcMBL (SEQ ID NO. 7):
AKTEPKSSDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GAPDGDSSLA

ASERKALQTE MARIKKWLTF SLGKQVGNKF FLTNGEIMTF

EKVKALCVKF QASVATPRNA AENGAIQNLI KEEAFLGITD

EKTEGQFVDL TGNRLTYTNW NEGEPNNAGS DEDCVLLLKN

GQWNDVPCST SHLAVCEFPI (viii)
FcMBL.111 (SEQ ID NO. 8):
EPKSSDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GATSKQVGNKF

FLTNGEIMTF EKVKALCVKF QASVATPRNA AENGAIQNLI

KEEAFLGITD EKTEGQFVDL TGNRLTYTNW NEGEPNNAGS

DEDCVLLLKN GQWNDVPCST SHLAVCEFPI
```

In some embodiments, microbe-binding molecule comprises an amino acid sequence selected from SEQ ID NO. 1-SEQ ID NO. 8.

In some embodiments, the label probe is conjugated to at least one reporter enzyme, as described herein. A label probe and a reporter enzyme can be linked to each other by a linker. In some embodiments, the linker between the label probe and the reporter enzyme is an amide bond. In some embodiments, the linker between the label probe and the enzyme is a disulfide (S—S) bond.

As used herein, the term "linker" generally refers to a molecular entity that can directly or indirectly connect two parts of a composition, e.g., at least one target-binding molecule and at least one substrate-binding domain or at least one enzyme and at least one target-binding molecule. In some embodiments, the linker can directly or indirectly connect to one or more target-binding molecules or target-binding domains.

Linkers can be configured according to a specific need, e.g., based on at least one of the following characteristics. By way of example only, in some embodiments, linkers can be configured to have a sufficient length and flexibility such that it can allow for a target analyte surface-binding domain to orient accordingly with respect to at least one carbohydrate on a microbe surface. In some embodiments, linkers can be configured to allow multimerization of at least two engineered target-binding molecules (e.g., to from a di-, tri-, tetra-, penta-, or higher multimeric complex) while retaining biological activity (e.g., microbe-binding activity). In some embodiments, linkers can be configured to facilitate expression and purification of the engineered target- or microbe-binding molecule described herein. In some embodiments, linkers can be configured to provide at least one recognition-site for proteases or nucleases. In addition, linkers should be non-reactive with the functional components of the engineered molecule described herein (e.g., minimal hydrophobic or charged character to react with the functional protein domains such as a microbe surface-binding domain or a substrate-binding domain).

In some embodiments, a linker can be configured to have any length in a form of a peptide, a protein, or any combinations thereof. In some embodiments, the peptide linker can vary from about 1 to about 1000 amino acids long, from about 10 to about 500 amino acids long, from about 30 to about 300 amino acids long, or from about 50 to about 150 amino acids long. Longer or shorter linker sequences can be also used for the engineered target- or microbe-binding molecules described herein. In one embodiment, the peptide linker has an amino acid sequence of about 200 to 300 amino acids in length.

In some embodiments, a peptide linker can be configured to have a sequence comprising at least one of the amino acids selected from the group consisting of glycine (Gly), serine (Ser), asparagine (Asn), threonine (Thr), methionine (Met) or alanine (Ala), or at least one of codon sequences encoding the aforementioned amino acids (i.e., Gly, Ser, Asn, Thr, Met or Ala). Such amino acids and corresponding nucleic acid sequences are generally used to provide flexibility of a linker. However, in some embodiments, other uncharged polar amino acids (e.g., Gln, Cys or Tyr), non-polar amino acids (e.g., Val, Leu, Ile, Pro, Phe, and Trp), or nucleic acid sequences encoding the amino acids thereof can also be included in a linker sequence. In alternative embodiments, polar amino acids can be added to modulate the flexibility of a linker. One of skill in the art can control flexibility of a linker by varying the types and numbers of residues in the linker See, e.g., Perham, 30 Biochem. 8501 (1991); Wriggers et al., 80 Biopolymers 736 (2005).

In alternative embodiments, a linker can be a chemical linker of any length. In some embodiments, chemical linkers can comprise a direct bond or an atom such as oxygen or sulfur, a unit such as NH, C(O), C(O)NH, SO, $SO_2$, $SO_2NH$, or a chain of atoms, such as substituted or unsubstituted C1-C6 alkyl, substituted or unsubstituted C2-C6 alkenyl, substituted or unsubstituted C2-C6 alkynyl, substituted or unsubstituted C6-C12 aryl, substituted or unsubstituted C5-C12 heteroaryl, substituted or unsubstituted C5-C12 heterocyclyl, substituted or unsubstituted C3-C12 cycloalkyl, where one or more methylenes can be interrupted or terminated by O, S, S(O), $SO_2$, NH, or C(O). In some embodiments, the chemical linker can be a polymer chain (branched or linear).

In some embodiments where the linker is a peptide, such peptide linker can comprise at least a portion of an immunoglobulin, e.g., IgA, IgD, IgE, IgG and IgM including their subclasses (e.g., IgG1), or a modified thereof. In some embodiments, the peptide linker can comprise a portion of fragment crystallization (Fc) region of an immunoglobulin or a modified thereof. In such embodiments, the portion of the Fc region that can be used as a linker can comprise at least one region selected from the group consisting of a hinge region, a $CH_2$ region, a $CH_3$ region, and any combinations thereof. By way of example, in some embodiments, a $CH_2$ region can be excluded from the portion of the Fc region as a linker. In one embodiment, Fc linker comprises a hinge region, a $CH_2$ domain and a $CH_3$ domain. Such Fc linker can be used to facilitate expression and purification of the engineered microbe-binding molecules described herein. The N terminal Fc has been shown to improve expression levels, protein folding and secretion of the fusion partner. In addition, the Fc has a staphylococcal protein A binding site, which can be used for one-step purification protein A affinity chromatography. See Lo K M et al. (1998) Protein Eng. 11: 495-500. Further, such Fc linker have a molecule weight above a renal threshold of about 45 kDa, thus reducing the possibility of engineered microbe-binding molecules being removed by glomerular filtration. Additionally, the Fc linker can allow dimerization of two engineered microbe-binding molecules to form a dimer, e.g., a dimeric MBL molecule.

In various embodiments, the N-terminus or the C-terminus of the linker, e.g., the portion of the Fc region, can be modified. By way of example only, the N-terminus or the C-terminus of the linker can be extended by at least one additional linker described herein, e.g., to provide further flexibility, or to attach additional molecules. In some embodiments, the N-terminus of the linker can be linked directly or indirectly (via an additional linker) with a substrate-binding domain adapted for orienting the carbohydrate recognition domain away from the substrate. Exemplary Fc linked MBL (FcMBL and Akt-FcMBL) are described in PCT application no. PCT/US2011/021603, filed Jan. 19, 2011, content of which is incorporated herein by reference.

In some embodiments, the linker can be embodied as part of the microbe surface-binding domain.

In some embodiments, the distance between the microbe surface-binding domain and the substrate surface can range from about 50 angstroms to about 5000 angstroms, from about 100 angstroms to about 2500 angstroms, or from about 200 angstroms to about 1000 angstroms.

In some embodiments, the linkers can be branched. For branched linkers, the linker can link together at least one (e.g., one, two, three, four, five, six, seven, eight, nine, ten or more) surface binding domain and at least one (e.g., one, two, three, four, five, six, seven, eight, nine, ten or more) microbe surface-binding domain.

When the label probe is a peptide, polypeptide or a protein, the enzyme can be linked at the N-terminus, the C-terminus, or at an internal position of the microbe-binding molecule. Similarly, the enzyme can be linked by its N-terminus, C-terminus, or an internal position.

In some embodiments, the capture probe can be affixed to a solid substrate described herein to form a target-binding substrate. Non-limiting examples of a solid substrate include, but are not limited to, an electrode (e.g. an analyte-specific electrode), a nanoparticle, a nanotube, sensor, a protein scaffold, a lipid scaffold, a dendrimer, microparticle or a microbead, a microtiter plate, a medical apparatus or implant, a microchip, and any combinations thereof.

The solid substrate can be made of any material, including, but not limited to, metal, metal alloy, polymer, plastic, paper, glass, fabric, packaging material, biological material such as cells, tissues, hydrogels, proteins, peptides, nucleic acids, and any combinations thereof.

Additional material that can be used to fabricate or coat a solid substrate include, without limitations, polydimethylsiloxane, polyimide, polyethylene terephthalate, polymethylmethacrylate, polyurethane, polyvinylchloride, polystyrene polysulfone, polycarbonate, polymethylpentene, polypropylene, polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly (ethylene glycol), styrene-acrylonitrile resin, poly(trimethylene terephthalate), polyvinyl butyral, polyvinylidenedifluoride, poly(vinyl pyrrolidone), and any combination thereof.

A solid substrate surface can be functionalized or activated for conjugation with capture probes by any methods known in the art. Exemplary conjugations include, but are not limited to, a linker as described herein, a covalent bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, temperature sensitive, radiation (IR, near-IR, UV) sensitive bond or conjugation agent, pH-sensitive bond or conjugation agent, non-covalent bonds (e.g., ionic charge complex formation, hydrogen bonding, pi-pi interactions, cyclodextrin/adamantly host guest interaction) and the like. In some embodiments, a solid substrate surface can be functionalized with addition of silane coupling agents (e.g., but not limited to organosilanes, aminosilanes, vinyl silanes, methacryl silanes, and any combinations thereof).

In some embodiments, the target-binding agents can comprise target-binding nanoparticles. As used herein, the term "target-binding nanoparticles" refers to nanoparticles conjugated to capture probes for specific binding with a target analyte.

In some embodiments, the target-binding nanoparticles can be magnetic (e.g., paramagnetic, superparamagnetic, or ferromagnetic). For example, the target-binding nanoparticles can be paramagnetic or superparamagnetic. The target-binding nanoparticles can range in size from 1 nm to 1000 nm. For example, the target-binding nanoparticles can be about 2.5 nm to about 500 nm, or about 5 nm to about 250 nm in size. In some embodiments, the target-binding nanoparticles can be about 5 nm to about 100 nm in size. In some embodiments, the target-binding nanoparticles can be about 0.01 nm to about 10 nm in size. In some embodiments, the target-binding nanoparticles can be about 0.05 nm to about 5 nm in size. In some embodiments, the target-binding nanoparticles can be about 80 nm to about 1000 nm in size. In some embodiments, the target-binding nanoparticles can have a size ranging from about 1 nm to about 1000 nm, from about 10 nm to about 500 nm, from about 25 nm to about 300 nm, from about 40 nm to about 250 nm, or from about 50 nm to about 200 nm. In one embodiment, the target-binding nanoparticles can have a size of about 50 nm to about 200 nm. The target-binding magnetic nanoparticles can be manipulated using magnetic field or magnetic field gradient. Such particles commonly consist of magnetic elements such as iron, nickel and cobalt and their oxide compounds. Magnetic microbeads are well-known and methods for their preparation have been described in the art. See, e.g., U.S. Pat. No. 6,878,445; No. 5,543,158; No. 5,578,325; No. 6,676,729; No. 6,045,925; and No. 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199, the contents of which are incorporated herein by reference.

The target-binding nanoparticles can be of any shape, including but not limited to spherical, rod, elliptical, cylindrical, and disc. The nanoparticles can be of any shape, e.g., a sphere. In some embodiments, the term "nanoparticle" as used herein can encompass a nanosphere. The term "nanosphere" as used herein refers to a nanoparticle having a substantially spherical form. A substantially spherical nanoparticle is a nanoparticle with a difference between the smallest radii and the largest radii generally not greater than about 40% of the smaller radii, and more typically less than about 30%, or less than 20%.

The capture probe or label probe can be present in any form, including but not limited to a target-binding molecule, and/or a target-binding substrate (e.g., a target-binding molecule conjugated to a solid substrate) as described above. By "target-binding molecules" is meant herein molecules that can interact with or bind to a target analyte such that the target analyte can be captured or detected from a fluid sample. Typically the nature of the interaction or binding is noncovalent, e.g., by hydrogen, electrostatic, or van der Waals interactions, however, binding can also be covalent. Target-binding molecules can be naturally-occurring, recombinant or synthetic. Examples of the target-binding molecule can include, but are not limited to an antibody or a portion thereof, an antibody-like molecule, an enzyme, an antigen, a small molecule, a protein, a peptide, a peptido-mimetic, a carbohydrate, an aptamer, and any combinations thereof. By way of example only, in immunohistochemistry, the target-binding molecule can be an antibody specific to the target antigen to be analyzed. An ordinary artisan can readily identify appropriate target-binding molecules for each target species or analytes of interest to be detected in various bioassays.

In some embodiments, the target-binding molecules can be modified by any means known to one of ordinary skill in the art. Methods to modify each type of target-binding molecules are well recognized in the art. Depending on the types of target-binding molecules, an exemplary modification includes, but is not limited to genetic modification, biotinylation, labeling (for detection purposes), chemical modification (e.g., to produce derivatives or fragments of the target-binding molecule), and any combinations thereof. In some embodiments, the target-binding molecule can be genetically modified. In some embodiments, the target-binding molecule can be biotinylated. In some embodiments, the label probe is functionalized with biotin and at least one reporter enzyme is conjugated to streptavidin. After the target analyte is bound to the capture probes on the analyte-specific electrode, the target analyte complex is labeled with the biotinylated label probe. Then, the streptavidin conjugated to at least one reporter enzyme binds to the biotin-functionalized label probe. In some embodiments, streptavidin may be conjugated with 1, 2, 3, 4, 5, 6, 7, 8, 9, 10 or more reporter enzymes. Reporter enzymes that can be conjugated to streptavidin include, but are not limited to, horseradish peroxidase (HRP), alkaline phosphatase (AP), glucose oxidase (GOx), tyrosinase, urease, a DNAzyme, an aptazyme, or any combinations thereof.

In some embodiments, the target-binding molecules can comprise on their surfaces microbe-binding molecules as described herein, and/or disclosed in WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), the contents of which are incorporated herein by reference. Accordingly, in some embodiments, the method described herein can be used with the target-binding nanoparticles for microbial capture, i.e., microbe-binding nanoparticles, e.g., but not limited to FcMBL-coated nanoparticles. In some embodiments, the nanoparticles are magnetic. Examples of microbe-binding magnetic particles can include, but are not limited to the ones described in WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), the contents of which are incorporated herein by reference.

In some embodiments, the target-binding molecule can be an antibody or a portion thereof, or an antibody-like molecule. In some embodiments, the target-binding molecule can be an antibody or a portion thereof, or an antibody-like molecule that is specific for detection of a rare-cell, e.g., a circulating tumor cell, a fetal cell, a stem cell and/or a microbe biomarker. In some embodiments, the target-binding molecule can be an antibody or a portion thereof, or an antibody-like molecule that is specific for a protein or an antigen present on the surface of a rare cell, e.g., a circulating tumor cell, a fetal cell, a stem cell and/or a microbe. In such embodiments, the target-binding molecules can be used to, for example, detect and/or identify cell type or species (including normal and/or diseased cells), the presence of cell or disease markers, cellular protein expression levels, phosphorylation or other post-translation modification state, or any combinations thereof.

In some embodiments, the target-binding molecule can be a protein or a peptide. In some embodiments, the protein or peptide can be essentially any proteins that can bind to a rare cell, e.g., a circulating tumor cell, a fetal cell, a stem cell and/or a microbe. By way of example only, if the target species is a bacteria, exemplary proteins or peptides that can be used to generate microbe-binding molecules and/or microbe-binding magnetic particles can include, but are not limited to, innate-immune proteins (e.g., without limitations, MBL, Dectin-1, TLR2, and TLR4 and any molecules (including recombinant or engineered protein molecules) disclosed here as well as the microbe-binding molecules disclosed in the International Application Publication Nos. WO/2011/090954 and WO/2013/012924, the content of which is incorporated herein by reference) and proteins comprising the chitin-binding domain, and any factions thereof. Such innate-immune proteins and chitin-binding domain proteins can be used to detect their corresponding pattern-recognition targets (e.g., microbes such as bacteria) and fungus, respectively.

In some embodiments, the target-binding molecule can be an aptamer. In some embodiments, the target-binding molecule can be a DNA or RNA aptamer. The aptamers can be used in various bioassays, e.g., in the same way as antibodies or nucleic acids described herein. For example, the DNA or RNA aptamer can encode a nucleic acid sequence corresponding to a rare cell biomarker or a fraction thereof, for use as a target-binding molecule on the nanoparticles described herein.

In some embodiments, the target-binding molecule can be a cell surface receptor ligand. As used herein, a "cell surface receptor ligand" refers to a molecule that can bind to the outer surface of a cell. Exemplary cell surface receptor ligand includes, for example, a cell surface receptor binding peptide, a cell surface receptor binding glycopeptide, a cell surface receptor binding protein, a cell surface receptor binding glycoprotein, a cell surface receptor binding organic compound, and a cell surface receptor binding drug. Additional cell surface receptor ligands include, but are not limited to, cytokines, growth factors, hormones, antibodies, and angiogenic factors. In some embodiments, any art-recognized cell surface receptor ligand that can bind to a rare cell, e.g., a circulating tumor cell, a fetal cell, a stem cell and/or a microbe, can be used as a target-binding molecule on the magnetic particles described herein.

In accordance with various embodiments described herein, a sample, including any fluid or specimen (processed or unprocessed) that is intended to be evaluated for the presence of a target analyte can be subjected to methods, compositions, kits and systems described herein. The sample or fluid can be liquid, supercritical fluid, solutions, suspensions, gases, gels, slurries, and combinations thereof. The sample or fluid can be aqueous or non-aqueous.

In some embodiments, the sample can be an aqueous fluid. As used herein, the term "aqueous fluid" refers to any flowable water-containing material that is suspected of comprising a pathogen.

In some embodiments, the sample can include a biological fluid obtained from a subject. Exemplary biological fluids obtained from a subject can include, but are not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied stool sample, synovial fluid, lymphatic fluid, tears, tracheal aspirate, and any mixtures thereof. In some embodiments, a biological fluid can include a homogenate of a tissue specimen (e.g., biopsy) from a subject. In one embodiment, a test sample can comprises a suspension obtained from homogenization of a solid sample obtained from a solid organ or a fragment thereof.

In some embodiments, the sample can be a whole blood sample obtained from a subject suspected of having a microbe infection (e.g., a pathogen infection).

In some embodiments, the sample can include a fluid or specimen obtained from an environmental source. For example, the fluid or specimen obtained from the environmental source can be obtained or derived from food products or industrial food products, food produce, poultry, meat, fish, beverages, dairy products, water (including wastewater), surfaces, ponds, rivers, reservoirs, swimming pools, soils, food processing and/or packaging plants, agricultural places, hydrocultures (including hydroponic food farms), pharmaceutical manufacturing plants, animal colony facilities, and any combinations thereof.

In some embodiments, the sample can include a fluid or specimen collected or derived from a biological culture. For example, a biological culture can be a cell culture. Examples of a fluid or specimen collected or derived from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof. In some embodiments, the test sample can include a fluid from a blood culture. In some embodiments, the culture medium can be obtained from any source, e.g., without limitations, research laboratories, pharmaceutical manufacturing plants, hydrocultures (e.g., hydroponic food farms), diagnostic testing facilities, clinical settings, and any combinations thereof.

In some embodiments, the sample can be a fluid or specimen collected or derived from a microbe colony.

In some embodiments, the sample can include a media or reagent solution used in a laboratory or clinical setting, such as for biomedical and molecular biology applications. As used herein, the term "media" refers to a medium for maintaining a tissue, an organism, or a cell population, or refers to a medium for culturing a tissue, an organism, or a cell population, which contains nutrients that maintain viability of the tissue, organism, or cell population, and support proliferation and growth.

As used herein, the term "reagent" refers to any solution used in a laboratory or clinical setting for biomedical and molecular biology applications. Reagents include, but are not limited to, saline solutions, PBS solutions, buffered solutions, such as phosphate buffers, EDTA, Tris solutions, and any combinations thereof. Reagent solutions can be used to create other reagent solutions. For example, Tris solutions and EDTA solutions are combined in specific ratios to create "TE" reagents for use in molecular biology applications.

In some embodiments, the sample can be a non-biological fluid. As used herein, the term "non-biological fluid" refers to any fluid that is not a biological fluid as the term is defined herein. Exemplary non-biological fluids include, but are not limited to, water, salt water, brine, buffered solutions, saline solutions, sugar solutions, carbohydrate solutions, lipid solutions, nucleic acid solutions, hydrocarbons (e.g. liquid hydrocarbons), acids, gasolines, petroleum, liquefied samples (e.g., liquefied samples), and mixtures thereof.

Advantageously, the methods described herein are useful for detecting very low amounts and/or concentrations of one or more target analytes in a sample. In some embodiments, the method comprises mixing a sample comprising the target analyte(s) with a plurality of nanoparticles, wherein the nanoparticles are functionalized as described herein with one or more types of capture probes, each type of capture probe being specific for binding with one target analyte, and allowing the target analyte(s) to bind with the capture probes on the nanoparticles. Binding the target analyte to nanoparticles prior to detection increases the sensitivity of the assay. Then, the sample comprising the target analyte bound to nanoparticles is introduced into an electrochemical sensor comprising a fluid-contact surface and one or more analyte-specific electrodes immobilized on at least a portion of the fluid-contact surface, wherein the analyte-specific electrode is functionalized with a capture probe for specific binding with the target analyte. Next, the target analyte bound to nanoparticles is allowed to bind with the capture probe on the analyte-specific electrode, thereby forming a complex comprising nanoparticle, target analyte and capture probe on a surface of the analyte-specific electrode. Next, the complex is labeled with a label probe, wherein the label probe binds specifically with the target analyte and the label probe is conjugated with at least one reporter enzyme. Next, an electroactive mediator precipitating composition is introduced into the electrochemical sensor, wherein a reaction of the electroactive mediator precipitating composition with the at least one reporter enzyme conjugated with the label probe forms an electroactive precipitate locally adsorbed at the surface of the analyte-specific electrode. Then a voltage is applied to the electrochemical sensor, wherein the voltage corresponds to the standard redox potential of the electroactive precipitate, and a current generated from the analyte-specific electrode of the electrochemical sensor is measured to detect the target analyte.

The methods described herein can be used to diagnose an illness in a patient. Non-limiting examples include detection of a microbe in a blood sample, which can be used to diagnose a patient with an infection. Another non-limiting example includes detection of abnormal cells in a blood sample (e.g., cancer cells). The methods described herein can also be used to detect microbes in food, water, the environment, etc.

In the methods described herein, it can be necessary or desired that a sample is preprocessed prior to being introduced into an electrochemical sensor as described herein, e.g., with a preprocessing reagent. Even in cases where pretreatment is not necessary, preprocessing optionally can be done for mere convenience (e.g., as part of a regimen on a commercial platform). A preprocessing reagent can be any reagent appropriate for use with the methods described herein.

The sample preprocessing step generally comprises adding one or more reagents to the sample. This preprocessing can serve a number of different purposes, including, but not limited to, hemolyzing cells such as blood cells, dilution of sample, etc. The preprocessing reagents can be present in the sample container before sample is added to the sample container or the preprocessing reagents can be added to a sample already present in the sample container. When the sample is a biological fluid, the sample container can be a VACUTAINER®, e.g., a heparinized VACUTAINER®.

The preprocessing reagents include, but are not limited to, surfactants and detergents, salts, cell lysing reagents, anti-coagulants, degradative enzymes (e.g., proteases, lipases, nucleases, lipase, collagenase, cellulases, amylases and the like), and solvents, such as buffer solutions.

In some embodiments, a preprocessing reagent is a surfactant or a detergent. In one embodiment, the preprocessing reagent is Triton X100.

After addition of the preprocessing reagent, the reagent can be mixed into the sample. This can be simply accomplished by agitating the sample, e.g., shaking the sample and/or moving the sample around in a microfluidic device.

After the optional preprocessing step, the sample can be optionally further processed by adding one or more processing reagents to the sample. These processing reagents can degrade unwanted molecules present in the sample and/or dilute the sample for further processing. These processing reagents include, but are not limited to, surfactants and detergents, salts, cell lysing reagents, anticoagulants, degradative enzymes (e.g., proteases, lipases, nucleases, lipase, collagenase, cellulases, amylases, heparanases, and the like), and solvents, such as buffer solutions. Amount of the processing reagent to be added can depend on the particular sample to be analyzed, the time required for the sample analysis, identity of the microbe to be detected or the amount of microbe present in the sample to be analyzed.

It is not necessary, but if one or more reagents are to be added they can present in a mixture (e.g., in a solution, "processing buffer") in the appropriate concentrations. Amount of the various components of the processing buffer can vary depending upon the sample, microbe to be detected, concentration of the microbe in the sample, or time limitation for analysis.

Generally, addition of the processing buffer can increase the volume of the sample by 5%, 10%, 15%, 20% or more. In some embodiments, about 50 µl to about 500 µl of the processing buffer are added for each ml of the sample. In some embodiments, about 100 µl to about 250 µl of the processing buffer are added for each ml of the sample. In one embodiment, about 125 µl of the processing buffer are added for each ml of the sample.

In some embodiments, a detergent or surfactant comprises about 5% to about 20% of the processing buffer volume. In some embodiments, a detergent or surfactant comprises about 5% to about 15% of the processing buffer volume. In one embodiment, a detergent or surfactant comprises about 10% of the processing buffer volume.

In some embodiments, one mL of the processing buffer comprises about 1 U to about 100 U of a degradative enzyme. In some embodiments, one ml of the processing buffer comprises about 5 U to about 50 U of a degradative enzyme. In one embodiment, one ml of the processing buffer comprises about 10 U of a degradative enzyme. Enzyme unit (U) is an art known term for the amount of a particular enzyme that catalyzes the conversion of 1 µmol of substrate per minute.

In some embodiments, one ml of the processing buffer comprises about 1 µg to about 10 µg, or about 1 mg to about 10 mg of an anti-coagulant. In some embodiments, one ml of the processing buffer comprises about 1 µg to about 5 µg, or about 1 mg to about 5 mg of an anti-coagulant. In one embodiment, one ml of the processing buffer comprises about 4.6 µg, or about 4.6 mg of an anti-coagulant.

Exemplary anti-coagulants include, but are not limited to, heparin, heparin substitutes, salicylic acid, D-phenylalanyl-L-prolyl-L-arginine chloromethyl ketone (PPACK), Hirudin, ANCROD® (snake venom, VIPRONAX®), tissue plasminogen activator (tPA), urokinase, streptokinase, plasmin, prothrombopenic anticoagulants, platelet phosphodiesterase inhibitors, dextrans, thrombin antagonists/inhibitors, ethylene diamine tetraacetic acid (EDTA), acid citrate dextrose (ACD), sodium citrate, citrate phosphate dextrose (CPD), sodium fluoride, sodium oxalate, sodium polyanethol sulfonate (SPS), potassium oxalate, lithium oxalate, sodium iodoacetate, lithium iodoacetate and mixtures thereof.

Generally, salt concentration of the processing buffer can range from about 10 mM to about 100 mM. In some embodiments, the processing buffer comprises a salt at a concentration of about 25 mM to about 75 mM. In some embodiment, the processing buffer comprises a salt at a concentration of about 45 mM to about 55 mM. In one embodiment, the processing buffer comprises a salt at a concentration of about 43 mM to about 45 mM.

The processing buffer can be made in any suitable buffer solution known to a skilled artisan. In some embodiments, the buffer solution is physiologically compatible to cells. Alternatively, the processing buffer can be made in water.

In some embodiments, the processing buffer comprises a mixture of Triton-X, DNAse I, human plasmin, $CaCl_2$ and Tween-20. In one embodiment, the processing buffer consists of a mixture of Triton-X, DNAse I, human plasmin, $CaCl_2$ and Tween-20 in a TBS buffer.

In one embodiment, one ml of the processing buffer comprises 100 μl of Triton-X100, 10 μl of DNAse (1 U/1 μl), 10 μl of human plasmin at 4.6 mg/ml and 870 μl of a mixture of TBS, 0.1% Tween-20 and 50 mM $CaCl_2$.

After processing of the sample, the sample can be subjected to a target analyte capture process. The target analyte capture process can allow for concentrating and/or cleaning up the sample before proceeding with detection. The extraction and concentration process can be completed in less than 6 hours, less than 5 hours, less than 4 hours, less than 3 hours, less than 2 hours, less than 1 hour, less than 30 minutes, less than 15 minutes, less than 10 minutes, or shorter. In some embodiments, extraction and concentration of a target analyte in the sample can be done within 10 minutes to 60 minutes of starting the process. In some embodiments, extraction and concentration of a target analyte in the sample can be done in about 10 minutes, e.g., mixing a sample comprising a target analyte to be extracted with at least one target-binding substrate (e.g., a plurality of target-binding magnetic nanoparticles described herein) optionally followed by separation of the target-bound target-binding substrate from the rest of the sample.

Additionally, the extraction and concentration process described herein can be utilized to extract a target analyte in a sample of any given volume. In some embodiments, sample volume is about 0.25 ml to about 50 ml, about 0.5 ml to about 25 ml, about 1 ml to about 15 ml, about 2 ml to about 10 ml. In some embodiments, sample volume is about 5 ml. In one embodiment, sample volume is 8 ml.

In some embodiments, the target analyte capture process comprises mixing a solid substrate, the surface of which is coated with target-binding molecules which can bind to a target analyte in the sample. By "coated" is meant that a layer of target-binding molecules is present on a surface of the solid substrate and available for binding with a microbe. A solid substrate or a solid supporting structure coated with target-binding molecules is also referred to as a "target-binding substrate." For example, an analyte-specific electrode as described herein can be a target-binding substrate. The amount of the target-binding molecules used to coat a solid substrate surface can vary with a number of factors such as a solid substrate surface area, coating density, types of target-binding molecules, and binding performance. A skilled artisan can determine the optimum density of target-binding molecules on a solid substrate surface using any methods known in the art. By way of example only, the amount of the target-binding molecules used to coat a solid substrate can vary from about 1 wt % to about 30 wt % or from about 5 wt % to about 20 wt %. In some embodiments, the amount of the target-binding molecules used to coat the solid substrate can be higher or lower, depending on a specific need. However, it should be noted that if the amount of the target-binding molecules used to coat the substrate is too low, the target-binding substrate can show a lower binding performance with a target analyte. On the contrary, if the amount of the target-binding molecules used to coat the substrate is too high, the dense layer of the target-binding molecules can exert an adverse influence on the binding properties.

In some embodiments, the target-binding substrate is a particle, e.g., a nano- or micro-particle. In some embodiments, the target-binding molecule coated substrate is a MBL, a recombinant MBL, FcMBL or AKT-FcMBL coated bead, microbead or magnetic microbead as described in the International Application Publication Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), contents of both of which are incorporated herein by reference. In some embodiments, the target-binding substrate can be coated with antibodies, aptamers, or nucleic acids against specific microbes, lectin (e.g., but not limited to MBL), or any combinations thereof.

After addition of the target-binding substrate, the target-binding substrate can be mixed in the sample to allow target analytes to bind with the capture probe. This can be simply accomplished by agitating the sample, e.g., shaking the sample and/or moving the sample around in a microfluidic device.

The sample mixture may optionally be subjected to a target analyte separation process. Without wishing to be bound by a theory, in some embodiments, capture and separation of the bound target analytes from the sample can concentrate the target analytes. In some embodiments, capture and separation of the bound target analytes from the sample can deplete target analytes from a sample. In some embodiments, capture and separation of the bound target analytes from the sample can remove components which can interfere with the assay from the bound target analytes. Any method known in the art for separating the target-binding substrate from the sample can be employed.

For example, when the target-binding substrate is magnetic, e.g., a magnetic bead, a magnet can be employed to separate the substrate bound target analytes from the sample fluid. Without limitations, target analyte capture also can be carried out by non-magnetic means, for example, by coating microbe-binding molecules on non-magnetic solid substrates or scaffolds (e.g., beads, posts, fibers, filters, capillary tubes, etc.) and flow sample by these affinity substrates.

The skilled artisan is well aware of methods for carrying out magnetic separations. Generally, a magnetic field or magnetic field gradient can be applied to direct the magnetic beads. Optionally, the bound target analyte can be washed with a buffer to remove any leftover sample and unbound components. Without wishing to be bound by a theory, capture and separation of the bound target analytes from the sample can concentrate the target analytes and also remove components, which can interfere with the assay or process, from the test sample. In some embodiments, the magnetic field gradient can be generated by a magnetic field gradient generator described in the U.S. Provisional Application No. 61/772,360, entitled "Magnetic Separator."

In some embodiments, the capture or detection of a microbe from the biological fluid or other samples can be accomplished by a method that does not require the identity of the microbe to be known for capture or detection. This can be accomplished using a solid substrate coated with a broad-spectrum microbe-binding molecule for microbe extraction from the sample. For example, in their previous work, the inventors described a method for the extraction and concentration of microbes (e.g., pathogens) from blood that does not require prior identification of pathogen. See PCT Application No. PCT/US2011/021603, filed Jan. 19, 2011, content of which is incorporated herein by reference. The method is based on beads that are coated with mannose binding lectin (MBL) or a genetically engineered version of MBL (FcMBL or Akt-FcMBL). MBL is a key component of the innate immune system, which binds to carbohydrate structures containing mannose, N-acetyl glucosamine and fucose on the surface of microbes or pathogens and that are not found on mammalian cells. MBL binds to at least 36 species of bacteria (e.g. Gram positive: Staphylococci, MRSA, VRSA, Streptococci, *Clostridium*; Gram negative: *Pseudomonas, E. coli, Klebsiella,*), 17 viruses (e.g. CMV, HIV, Ebola, HSV, HepB), 20 fungi (e.g., *Candida, Aspergillus, Cryptococcus*), and 9 parasites (e.g. Malaria, *Schistosoma*), in addition to at least one molecular toxin (e.g., LPS endotoxin). Consequently, MBL can serve as a broad-spectrum capture reagent, allowing a wide range of microbes (e.g., pathogens) to be extracted and concentrated from blood samples or other biological fluids.

Accordingly, in some embodiments of the aspects described herein, microbe capture or detection from a biological sample or other sample is by substrate coated with a broad-spectrum microbe-binding molecule. For example, microbe capture or extraction from a biological sample is by magnetic micro- or nano-beads as described in the International Application Publication Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), contents of both of which are incorporated herein by reference.

A sample comprising at least one target analyte, optionally pre-treated or pre-mixed with capture probe functionalized nanoparticles, can be introduced into an electrochemical sensor to detect and/or analyze the presence of the target analyte(s). In some embodiments, the electrochemical sensor comprises at least one analyte-specific electrode on a fluid-contact surface therein, wherein the analyte-specific electrode is functionalized with a capture probe for specific binding with the target analyte. The target analytes are allowed to bind with the capture probe on the analyte-specific electrode, thereby forming a complex comprising the target analyte and the capture probe on a surface of the analyte-specific electrode. In some embodiments, label probes that can bind with the target analytes can then be used to label the target analytes for detection. As used herein, a "label probe" refers to a molecule that comprises a reporter enzyme and can bind with a target analyte. Label probes can include, but are not limited to, MBL or a portion thereof, FcMBL, AKT-FcMBL, wheat germ agglutinin, lectins, antibodies (e.g., gram-negative antibodies or gram-positive antibodies, antibiotics to specific microbial strains or species), antigen binding fragments of antibodies, aptamers, carbohydrate-binding proteins, peptides, polypeptides, cell-binding molecules, lipid-binding molecules, ligands (agonists or antagonists) of cell-surface receptors and the like.

In some embodiments, the label probe can comprise MBL or a target-binding molecule described herein. In one embodiment, the label probe comprises FcMBL. Without wishing to be bound by a theory, label probes based on MBL, and FcMBL in particular, attach selectively to a broad range of microbes, and so they enable the method described herein to detect the majority of blood-borne microbes with high sensitivity and specificity.

In some embodiments, the reporter enzyme comprises horseradish peroxidase (HRP), alkaline phosphatase (AP), glucose oxidase (GOx), tyrosinase, urease, a DNAzyme, a aptazyme, or any combination thereof.

In one embodiment, the label probe can comprise a MBL or a portion thereof, or a FcMBL molecule linked to a HRP. Conjugation of HRP to any proteins and antibodies are known in the art. In one embodiment, FcMBL-HRP construct is generated by direct coupling HRP to FcMBL using any commercially-available HRP conjugation kit. In some embodiments, the target analytes bound on an analyte-specific electrode can be incubated with the HRP-labeled target-binding molecules, e.g., MBL or a portion thereof, or a FcMBL molecule linked to a HRP for a period of time, e.g., at least about 5 mins, at least about 10 mins, at least about 15 mins, at least about 20 mins, at least about 25 mins, at least about 30 mins. The typical concentrations of HRP-labeled molecules used in the assay can range from about 1:500 to about 1:20,000 dilutions. In one embodiment, the concentration of HRP-labeled label probes, e.g., MBL or a portion thereof, or a FcMBL molecule linked to a HRP molecule, can be about 1:1000 to about 1:10000 dilutions.

In one embodiment, the label probe can comprise a MBL or a portion thereof, or a FcMBL molecule linked to an AP. Conjugation of AP to any proteins and antibodies are known in the art. In one embodiment, FcMBL-AP construct is generated by direct coupling AP to FcMBL using any commercially-available AP conjugation kit. In some embodiments, the target analytes bound on an analyte-specific electrode can be incubated with the AP-labeled target-binding molecule, e.g., MBL or a portion thereof, or a FcMBL molecule linked to a AP for a period of time, e.g., at least about 5 mins, at least about 10 mins, at least about 15 mins, at least about 20 mins, at least about 25 mins, at least about 30 mins. The typical concentrations of AP-labeled molecules used in the assay can range from about 1:1000 to about 1:20,000 dilutions. In one embodiment, the concentration of AP-labeled target-binding molecules, e.g., MBL or a portion thereof, or a FcMBL molecule linked to a AP molecule, can be about 1:5000 to about 1:10000 dilutions.

Following incubation with the label probe, the analyte-specific electrodes may optionally be washed with a wash buffer one or more (e.g., 1, 2, 3, 4, 5 or more) times to remove any unbound probes. In some embodiments, the wash buffer used after incubation with a label probe can contain calcium ions at a concentration of about at least about 0.01 mM, at least about 0.05 mM, at least about 0.1 mM, at least about 0.5 mM, at least about 1 mM, at least about 2.5 mM, at least about 5 mM, at least about 10 mM, at least about 20 mM, at least about 30 mM, at least about 40 mM, at least about 50 mM or more. In alternative embodiments, the wash buffer used after incubation with a label probe can contain no calcium ions. In some embodiments, the wash buffer used after incubation with a label probe can contain a chelating agent. A wash buffer can be any art-recognized buffer used for washing between incubations with antibodies and/or labeling molecules. An exemplary wash buffer can include, but is not limited to, phosphate-buffered saline (PBS), Tris-buffered saline (TBS), TBST, a mixture of TBS, 0.1% Tween and 5 mM Ca2+, and any combination thereof.

The amount of calcium ions (Ca2+) present in the processing buffer and/or wash buffer can vary from about 1 mM to about 100 mM, from about 3 mM to about 50 mM, or from about 5 mM to about 25 mM. Calcium ions can be obtained from any calcium salts, e.g., but not limited to, $CaCl_2$, $CaBr_2$, $CaI_2$, and $Ca(NO_3)_2$, and any other art-recognized calcium salts. Without wishing to be bound by theory, the presence of calcium ions in the processing buffer and/or wash buffer can facilitate and/or maintain calcium-dependent binding (e.g., lectin-mediated binding such as MBL-mediated binding) of the microbe to a microbe-binding substrate.

In some embodiments, the wash buffer can exclude calcium ions and/or include a chelator, e.g., but not limited to, EDTA. In such embodiments, microbes that solely depend on calcium-dependent binding (e.g., lectin-mediated binding such as MBL-mediated binding) to the microbe-binding substrate will less likely bind to the microbe-binding substrate in the absence of calcium ions. However, microbes (e.g., pathogens such as S. aureus) that at least partly depend on non-calcium-dependent interaction (e.g., but not limited to, protein A/Fc-mediated binding) with the microbe-binding substrate (e.g., FcMBL-coated magnetic particles) can bind to the microbe-binding substrate in the absence of calcium ions, and additional information can be found, e.g., in the International Application Publication No. WO/2013/012924, or in the U.S. Provisional App. No. 61/605,052 filed Feb. 29, 2012, the content of which is incorporated herein by reference.

In some embodiments, without wishing to be bound by theory, it can be desirable to use a wash buffer without a surfactant or a detergent for the last wash before addition of the electroactive mediator precipitating composition, because a surfactant or detergent may have adverse effect to the enzymatic reaction with the enzyme substrate and electroactive mediator. The electrochemical sensor can optionally be washed any number (e.g., 1, 2, 3, 4, 5 or more) of times before detection. Without wishing to be bound by a theory, such washing can reduce and/or eliminate any contaminants from the biological fluid that can be problematic during detection.

In some embodiments, an electroactive mediator precipitating composition can be added to develop the assay. After the electroactive mediator composition reacts with reporter enzymes on the bound and labeled target analytes and forms an electroactive precipitate locally adsorbed at the surface of the analyte-specific electrodes, the electrochemical sensor may be optionally washed with wash buffer to remove any electroactive mediator precipitating composition or electroactive precipitate that is not adsorbed at the analyte-specific electrode surface. Any wash buffer as described herein may be used. An exemplary wash buffer can include, but is not limited to, phosphate-buffered saline (PBS), Tris-buffered saline (TBS), TBST, a mixture of TBS, 0.1% Tween and 5 mM Ca2+, and any combination thereof.

To detect any target analyte bound to the analyte-specific electrodes, a voltage is applied to the electrochemical sensor, wherein the voltage corresponds to the standard redox potential of the electroactive precipitate locally adsorbed at the surface of the analyte-specific electrode. Then, a current generated from the analyte-specific electrode of the electrochemical sensor is measured to detect the target analyte. Without being bound by theory, the voltage applied to the electrochemical sensor corresponds to an electrochemical reduction or oxidation potential of the electroactive mediator in a fully or partially oxidized state, and the generated current corresponds to a reduction or oxidation current derived from reduction or oxidation of the oxidized electroactive mediator. In some embodiments, the voltage applied is about −0.2V to +0.2V versus a reference electrode.

Any processes or steps described herein can be performed by a module or device. While these are discussed as discrete processes, one or more of the processes or steps described herein can be combined into one system for carrying out the assays of any aspects described herein. In some embodiments, the assay or process described herein can be adapted for use in a high-throughput platform, e.g., an automated system or platform.

In addition to the above mentioned components, any embodiments of the kits described herein can include informational material. The informational material can be descriptive, instructional, marketing or other material that relates to the methods described herein and/or the use of the aggregates for the methods described herein. For example, the informational material can describe methods for using the kits provided herein to perform an assay for capture and/or detection of a target analyte, e.g., a microbe. The kit can also include an empty container and/or a delivery device, e.g., which can be used to deliver a test sample to a test container.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments, the kit can contain separate containers, dividers or compartments for each component and informational material. For example, each different component can be contained in a bottle, vial, or syringe, and the informational material can be contained in a plastic sleeve or packet. In other embodiments, the separate elements of the kit are contained within a single, undivided container. For example, a collection of magnetic nanoparticles is contained in a bottle, vial or syringe that has attached thereto the informational material in the form of a label.

Exemplary embodiments of the invention are also described by one or more of the following numbered paragraphs:

1. A method for detecting a target analyte in a sample, comprising:
    (a) introducing a sample comprising a target analyte into an electrochemical sensor comprising a fluid-contact surface and an analyte-specific electrode immobilized on at least a portion of the fluid-contact surface, wherein the analyte-specific electrode is functionalized with a capture probe for specific binding with the target analyte;
    (b) allowing the target analyte to bind with the capture probe on the analyte-specific electrode, thereby forming a complex comprising the target analyte and the capture probe on a surface of the analyte-specific electrode;

(c) labeling the complex with a label probe, wherein the label probe binds specifically with the target analyte and the label probe is conjugated with at least one reporter enzyme;

(d) introducing an electroactive mediator precipitating composition into the electrochemical sensor, wherein a reaction of the electroactive mediator precipitating composition with the at least one reporter enzyme conjugated with the label probe forms an electroactive precipitate locally adsorbed at the surface of the analyte-specific electrode;

(e) applying a voltage to the electrochemical sensor, wherein the voltage corresponds to the standard redox potential of the electroactive precipitate; and (f) measuring a current generated from the analyte-specific electrode of the electrochemical sensor to detect the target analyte;

wherein the target analyte is not a nucleic acid.

2. The method of paragraph 1, further comprising prior to step (a):
   i. mixing a sample comprising the target analyte with a plurality of nanoparticles, wherein at least one nanoparticle of said plurality of nanoparticles is functionalized with a capture probe for specific binding with the target analyte; and
   ii. allowing the target analyte to bind with the capture probe on said at least one nanoparticle.

3. The method of paragraph 1 or 2, wherein the electrochemical sensor comprises a plurality of analyte-specific electrodes immobilized on at least a portion of the fluid-contact surface, wherein each analyte-specific electrode in said plurality of analyte-specific electrodes is functionalized with a capture probe for specific binding with a specific target analyte.

4. The method of paragraph 3, wherein at least two of the analyte-specific electrodes are adapted to detect different target analytes.

5. The method of any one of paragraphs 1-4, wherein at least two different target analytes in the sample are detected.

6. The method of any one of paragraphs 1-5, wherein the target analyte is selected from the group consisting of a protein, a peptide, a polypeptide, a peptidomimetic, an antibody, an antibody fragment, an amino acid, a peptide aptamer, a peptidoglycan, a cell, microbial matter, a carbohydrate, an antigen, a lipid, a steroid, a hormone, a lipopolysaccharide, an endotoxin, a drug, a lipid-binding molecule, a cofactor, a small molecule, a toxin, and any combination thereof.

7. The method of paragraph 6, wherein the protein is a glycoprotein.

8. The method of paragraph 6, wherein the microbial matter is selected from the group consisting of bacteria, viruses, protozoa, fungi, yeast, microbes, parasites, any fragments thereof, and any combination thereof.

9. The method of paragraph 6, wherein the carbohydrate is selected from the group consisting of mannose, mannan, N-acetyl glucosamine, fucose, a monosaccharide, a disaccharide, a trisaccharide, a polysaccharide, and any combination thereof.

10. The method of any one of paragraphs 2-9 wherein the nanoparticle is a magnetic nanoparticle, a gold nanoparticle, a silver nanoparticle, a semiconductor nanoparticle, or a polymeric nanoparticle.

11. The method of any one of paragraphs 2-10, wherein at least two of the nanoparticles are functionalized with capture probes for specific binding with at least two different target analytes.

12. The method of any one of paragraphs 1-11, further comprising, prior to the step of applying the voltage to the electrochemical sensor, washing the electrochemical sensor to remove any electroactive mediator precipitating composition or electroactive precipitate that is not adsorbed at the analyte-specific electrode surface.

13. The method of any one of paragraphs 1-12, wherein the electrochemical sensor comprises one or more microfluidic flow cells.

14. The method of any one of paragraphs 1-13, wherein the electrochemical sensor comprises one or more open wells.

15. The method of any one of paragraphs 1-14, wherein the analyte-specific electrode is a planar or 3-dimensional electrode.

16. The method of any one of paragraphs 1-15, wherein the analyte-specific electrode comprises gold, silver, copper, platinum, aluminum, stainless steel, tungsten, indium tin oxide, titanium, lead, nickel, palladium, silicon, polyimide, parylene, benzocyclobutene, carbon, graphite, or any combination thereof.

17. The method of any one of paragraphs 1-16, wherein the fluid-contact surface further comprises a counter electrode and a reference electrode immobilized thereon.

18. The method of any one of paragraphs 1-17, wherein the fluid-contact surface further comprises a positive control electrode and/or a negative control electrode immobilized thereon.

19. The method of any one of paragraphs 1-18, wherein the voltage applied to the electrochemical sensor corresponds to an electrochemical reduction or oxidation potential of the electroactive mediator in a fully or partially oxidized state.

20. The method of any one of paragraphs 1-19, wherein the generated current corresponds to a reduction or oxidation current derived from reduction of the fully or partially oxidized electroactive mediator.

21. The method of any one of paragraphs 1-20, wherein the voltage window is about −0.2V to +0.2V versus a reference electrode.

22. The method of any one of paragraphs 1-21, wherein the fluid-contact surface is a non-electrically conductive surface.

23. The method of paragraph 22, wherein the non-electrically conductive surface comprises plastic, poly(carbonate) (PC), poly(methyl methacrylate) (PMMA), cyclic olefin polymers (COP), cyclic olefin copolymers (COC), silicon nitride, parylene, kapton, styrene-ethylene-butylene-styrene (SEBS), poly-dimethysiloxane (PDMS), polyimide, silicon dioxide, and any combination thereof.

24. The method of any one of paragraphs 1-23, wherein the capture probe and the label probe are independently selected from the group consisting of an antibody, an antibody fragment, a carbohydrate-binding protein, a peptide, a polypeptide, an aptamer, a cell-binding molecule, a lipid-binding molecule, a polynucleotide, a lipid, a carbohydrate, and any combination thereof.

25. The method of paragraph 24, wherein the target analyte comprises a microbe, and the capture probe and label probe comprise a carbohydrate binding protein, wherein the carbohydrate binding protein comprises a carbohydrate recognition domain of mannan-binding lectin (MBL).

26. The method of paragraph 25, wherein the carbohydrate recognition domain of MBL is conjugated to an Fc portion of an immunoglobin.

27. The method of any one of paragraphs 1-26, wherein said at least one reporter enzyme is conjugated to the label probe before the label probe binds to the target analyte complex.

28. The method of any one of paragraphs 1-26, wherein said at least one reporter enzyme is conjugated to the label probe after the label probe binds to the target analyte complex.

29. The method of any one of paragraphs 1-28, wherein the label probe is functionalized with biotin and said at least one reporter enzyme is conjugated to streptavidin.

30. The method of paragraph 29, wherein the label probe first binds to the target analyte complex, and then the streptavidin conjugated to said at least one reporter enzyme binds to the biotin functionalized label probe.

31. The method of any one of paragraphs 1-30, wherein the at least one reporter enzyme comprises horseradish peroxidase (HRP), alkaline phosphatase (AP), glucose oxidase (GOx), tyrosinase, urease, a DNAzyme, an aptazyme, or any combination thereof.

32. The method of paragraph 31, wherein the at least one reporter enzyme comprises HRP.

33. The method of any one of paragraphs 1-32, wherein the electroactive mediator precipitating composition comprises a reporter enzyme substrate and an electroactive mediator.

34. The method of paragraph 33, wherein the reporter enzyme substrate is selected from the group consisting of hydrogen peroxide, carbamide peroxide, nucleotides, oligonucleotides, RNA, DNA, phosphorylated peptides, phosphorylated proteins, phosphorylated small molecules, glucose, phenols, tyrosine, dopamine, catechol, urea, and any combination thereof.

35. The method of paragraph 34, wherein the reporter enzyme substrate is hydrogen peroxide.

36. The method of any one of paragraphs 33-35, wherein the electroactive mediator is selected from the group consisting of 3,3',5,5'-tetramethylbenzidine (TMB), o-phenylenediamine dihydrochloride (OPD), 2,2'-Azinobis [3-ethylbenzothiazoline-6-sulfonic acid] (ABTS), p-Nitrophenyl Phosphate (PNPP), 3,3'-diaminobenzidine (DAB), 4-chloro-1-naphthol (4-CN), 5-bromo-4-chloro-3-indolyl-phosphate (BCIP), nitro blue tetrazolium (NBT), methylene blue, hydroquinone, ferrocene derivatives, and any combination thereof.

37. The method of paragraph 36, wherein the electroactive mediator is TMB.

38. The method of any one of paragraphs 1-37, wherein the electroactive mediator precipitating composition further comprises a precipitating agent.

39. The method of paragraph 38, wherein the precipitating agent is selected from the group consisting of a water-soluble polymer, a pyrrolidinone polymer, a polyaniline, a polypyrrole, a polythiophene, alginic acid, methyl vinyl ether/maleic anhydride copolymer, dextran sulfate, carrageenan, and any combination thereof.

40. The method of paragraph 39, wherein the precipitating agent is a pyrrolidinone polymer.

41. A kit for electrochemical multiplex detection of a plurality of target analytes in a sample comprising:

(a) an electrochemical sensor comprising a fluid-contact surface and a plurality of analyte-specific electrodes immobilized on at least a portion of the fluid-contact surface, wherein the analyte-specific electrodes are each functionalized with a capture probe for binding a specific target analyte;

(b) a plurality of label probes, wherein each label probe is for binding a specific target analyte, and wherein each label probe is conjugated to at least one reporter enzyme or is functionalized to be conjugated to at least one reporter enzyme; and (c) an electroactive mediator precipitating composition comprising a reporter enzyme substrate, an electroactive mediator and a precipitating agent, wherein a reaction of the reporter enzyme substrate and the electroactive mediator with the reporter enzyme forms an electroactive precipitate locally adsorbed at the surface of the analyte-specific electrodes;

wherein none of the target analytes are nucleic acids.

42. The kit of paragraph 41, further comprising a plurality of nanoparticles, wherein at least one nanoparticle of said plurality of nanoparticles is functionalized with a capture probe for specific binding with a target analyte.

43. The kit of paragraph 42, wherein the nanoparticles are independently selected from a magnetic nanoparticle, a gold nanoparticle, a silver nanoparticle, a semiconductor nanoparticle, or a polymeric nanoparticle.

44. The kit of any one of paragraphs 41-43, wherein the electrochemical sensor comprises one or more open wells.

45. The kit of any one of paragraphs 41-44, wherein the electrochemical sensor comprises one or more microfluidic flow cells.

46. The kit of any one of paragraphs 41-45, wherein the capture probe and the label probe are independently selected from the group consisting of an antibody, an antibody fragment, a carbohydrate-binding protein, a peptide, a polypeptide, an aptamer, a cell-binding molecule, a lipid-binding molecule, and any combination thereof.

47. The kit of paragraph 46, wherein the target analyte comprises a microbe, and the capture probe and label probe comprise a carbohydrate binding protein, wherein the carbohydrate binding protein comprises a carbohydrate recognition domain of mannan-binding lectin (MBL).

48. The method of paragraph 47, wherein the carbohydrate recognition domain of MBL is conjugated to an Fc portion of an immunoglobin.

49. The kit of any one of paragraphs 41-48, wherein the label probes are functionalized with biotin and the reporter enzymes are conjugated to streptavidin, so that the label probes first bind to specific target analytes, and then the streptavidin conjugated to the reporter enzymes binds to the biotin functionalized label probes.

50. The kit of any one of paragraphs 41-49, wherein the at least one reporter enzyme comprises horseradish peroxidase (HRP), alkaline phosphatase (AP), glucose oxidase (GOx), tyrosinase, urease, a DNAzyme, a aptazyme, or any combination thereof.

51. The kit of paragraph 50, wherein the at least one reporter enzyme comprises HRP.

52. The kit of any one of paragraphs 41-51, wherein the electroactive mediator precipitating composition comprises a reporter enzyme substrate and an electroactive mediator.

53. The kit of paragraph 52, wherein the reporter enzyme substrate is selected from the group consisting of hydrogen peroxide, carbamide peroxide, nucleotides, oligonucleotides, RNA, DNA, phosphorylated peptides, phosphorylated proteins, phosphorylated small molecules, glucose, phenols, tyrosine, dopamine, catechol, urea, and any combination thereof.

54. The kit of paragraph 53, wherein the reporter enzyme substrate is hydrogen peroxide.

55. The kit of any one of paragraphs 41-54, wherein the electroactive mediator is selected from the group consisting of 3,3',5,5'-tetramethylbenzidine (TMB), o-phenylenediamine dihydrochloride (OPD), 2,2'-Azinobis [3-ethylbenzothiazoline-6-sulfonic acid] (ABTS), p-Nitrophenyl Phosphate (PNPP), 3,3'-diaminobenzidine (DAB), 4-chloro-1-naphthol (4-CN), 5-bromo-4-chloro-3-indolyl-phosphate (BCIP), nitro blue tetrazolium (NBT), methylene blue, hydroquinone, ferrocene derivatives, and any combination thereof.

56. The kit of paragraph 55, wherein the electroactive mediator is TMB.

57. The kit of any one of paragraphs 41-56, wherein the electroactive mediator precipitating composition further comprises a precipitating agent.

58. The kit of paragraph 57, wherein the precipitating agent is selected from the group consisting of a water-soluble polymer, a pyrrolidinone polymer, a polyaniline, a polypyrrole, a polythiophene, alginic acid, methyl vinyl ether/maleic anhydride copolymer, dextran sulfate, carrageenan, and any combination thereof.

59. The kit of paragraph 58, wherein the precipitating agent is a pyrrolidinone polymer.

60. An electrochemical sensor comprising:
   (a) a fluid-contact surface and a plurality of analyte-specific electrodes immobilized on at least a portion of the fluid-contact surface, wherein the analyte-specific electrodes are each functionalized with a capture probe for binding a specific target analyte;
   (b) a plurality of different nanoparticle-bound target analytes bound to the corresponding capture probes of the analyte-specific electrodes; and
   (c) an electroactive precipitate locally adsorbed at the surfaces of at least some of the analyte-specific electrodes, wherein the electroactive precipitate is formed from a reaction of an electroactive mediator precipitating composition comprising a reporter enzyme substrate, an electroactive mediator and a precipitating agent, with a reporter enzyme coupled to the nanoparticle-bound target analytes;
   wherein none of the target analytes are nucleic acids.

61. The electrochemical sensor of paragraph 60, wherein the reporter enzyme is coupled to the nanoparticle-bound target analytes by specific binding of a label probe to the corresponding nanoparticle-bound target analytes, wherein the label probe is conjugated to the reporter enzyme.

Some Selected Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one aspect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

As used interchangeably herein, the terms "microbes" and "pathogens" generally refer to microorganisms, including bacteria, fungi, protozoan, archaea, protists, e.g., algae, and a combination thereof. The term "microbes" also includes pathogenic microbes, e.g., bacteria causing diseases such as plague, tuberculosis and anthrax; protozoa causing diseases such as malaria, sleeping sickness and toxoplasmosis; fungi causing diseases such as ringworm, candidiasis or histoplasmosis; and bacteria causing diseases such as sepsis. The term "microbe" or "microbes" can also encompass non-pathogenic microbes, e.g., some microbes used in industrial applications.

In some embodiments, the term "microbe" or "microbes" also encompasses fragments of microbes, e.g., cell components of microbes, LPS, and/or endotoxin.

As used herein, the term "binding" or "bound" generally refers to a reversible binding of one agent or molecule to another agent or molecule via, e.g., van der Waals force, hydrophobic force, hydrogen bonding, and/or electrostatic force. The binding interaction between an agent or molecule and another agent or molecule can be described by a dissociation constant ($K_d$) or association constant (K).

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the disclosed embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

An electrode array consisting of 64 individually addressable 300 μm in diameter gold working electrodes sharing common reference and counter electrodes was fabricated using standard microfabrication technology. Borofloat wafers were successively coated with the lift off resist LOR20 and the imaging resist Shipley 2005. Following photopatterning of the electrode array design (AutoCAD, Autodesk Inc, USA), the gold electrode array pattern was revealed in developing solution CD30. Wafers were then successively coated with 10 nm of titanium used as metal adhesion layer, and 80 nm of gold. The unwanted resist was lifts off in Remover PG at 90° C. Finally, the electrode arrays were insulated with SU8-2002 and the connection pads, working, counter and reference electrodes revealed photo-lithographically before releasing individual electrode arrays using an automated diamond saw.

The electrochemical characterization of the electrode array was performed using a PGSTAT12 potentiostat (Metrohm AG, The Netherlands) and an Ag/AgCl wire reference electrode and a platinum counter electrode. All assays were realized using the on-chip reference and counter electrodes and all electrodes were addressed simultaneously using a dedicated 64-channel measuring system specifically developed. Simple microfluidic flow cells were fabricated using an Epilog Legend 36EXT (EPIX) to cut and drill 2 mm thick poly(methylmethacrylate) sheets and define the microfluidic channels in 100 μm thick medical grade double-sided adhesive tape (Adhesives Research Ltd., Ireland—ArCare 90880).

Each of the assay electrodes was individually coated with FcMBL. Approximately 10 μL of diluted nanoparticle-bound target analyte was injected into the microfluidics and incubated for 60 minutes at room temperature. Channels were subsequently flushed with 100 μL of TBS buffer before injecting 20 μL of HRP-labelled FcMBL label probe prepared at a concentration of 10 nM in buffer as well. Labelling of the electrode-bound complexes occurred over a period of 30 minutes at room temperature, before flushing the microfluidics with 100 μL of TBS buffer. The presence of HRP label was measured by fast chronoamperometry after injecting 20 of TMB Enhanced HRP membrane substrate (Diarect AG, Germany), incubated for 5 minutes, and washing with 100 μL of Tris buffer, before reading the array and measuring the reduction current derived from the reduction of the HRP-oxidized TMB at −0.2 V (vs. internal reference).

Data were processed using a Visual Basic macro running under MS Excel to treat the current traces recorded at the 64 electrodes. The current response at 500 ms was used as the signal. Limits of detection were taken as the concentration value corresponding to the averaged current response of the negative control sensors over the entire concentration range plus three times the averaged standard deviation.

Without being bound by theory, high background signal was found to originate from the active transport of the oxidised TMB ($TMB_{ox}$) during its injection in the microfluidic cell. However, due to the high TMB:HRP reaction kinetics and the fluid dynamics, the $TMB_{ox}$ generated at one electrode can be actively transported to the next electrode even minutes after the TMB injection, resulting in high background current. To limit the transport of $TMB_{ox}$ to adjacent electrodes, a precipitating TMB formulation was used. Precipitating TMB formulations are commonly used in immunohistochemistry and Western blotting, and typically contain additives such as alginic acid, methyl vinyl ether/maleic anhydride copolymer, dextran sulfate and/or carrageenan, which can readily precipitate $TMB_{ox}$. The precipitated TMB was found to conserve its electroactivity. More importantly, it formed a stable electroactive precipitate at the electrode surface that could not be dissolved in aqueous buffer at pH 7.4. Consequently, following the capture probe binding and HRP-labeling steps, the arrays were incubated for 5 minutes in precipitating TMB and flushed with 100 μL of Tris buffer before reading the array.

Example 2

Dilute samples of rare target analytes (e.g., proteins, carbohydrates, pathogens, pathogen fragments, endotoxins, etc.) can be detected electrochemically, as shown in FIG. 1. Electrochemical sensors, i.e. electrodes (FIG. 1A), are modified with bio-engineered mannan-binding lectin (FcMBL, FIG. 1B) capable of recognising mannan moieties present at the surface of pathogen cell wall and endotoxins. Upon exposure to a sample containing even low concentration of pathogens, pathogens/fragments/toxins will bind to the electrode surface (FIG. 1C). To quantify the amount bound, an enzyme (e.g. horseradish peroxidase (HRP)) modified FcMBL is introduced, which will further bind to the surface captured pathogen (FIG. 1D). The amount of HRP present, which is proportional to the amount of captured pathogen, is finally quantified using precipitating 3,3′,5,5′-tetramethylbenzidine (TMB). TMB in the presence of HRP and hydrogen peroxide, will become oxidized (FIG. 1E), complexing with the precipitating agent and finally precipitating at the electrode surface (FIG. 1F). Following a washing step, the precipitated TMB is electrochemically detected. Detection sensitivity is increased by preconcentrating the pathogen/ fragment/toxins using nanoparticles coated with FcMBL in a first step. As illustrated in FIG. 1F, not all pathogen/pathogen fragment/toxin will bind to the electrode surface due to mass transport limitations. Preconcentrating the pathogen/pathogen fragment/toxin in solution using nanoparticles and capturing the nanoparticle complexes at the electrode surface (FIG. 1H) will result in more RhMBL-HRP binding to the electrode surface (FIG. 1I), a larger amount of TMB being oxidized and precipitating at the electrode surface (FIG. 1J), and consequently a higher detection signal.

Example 3

Figure 2A:
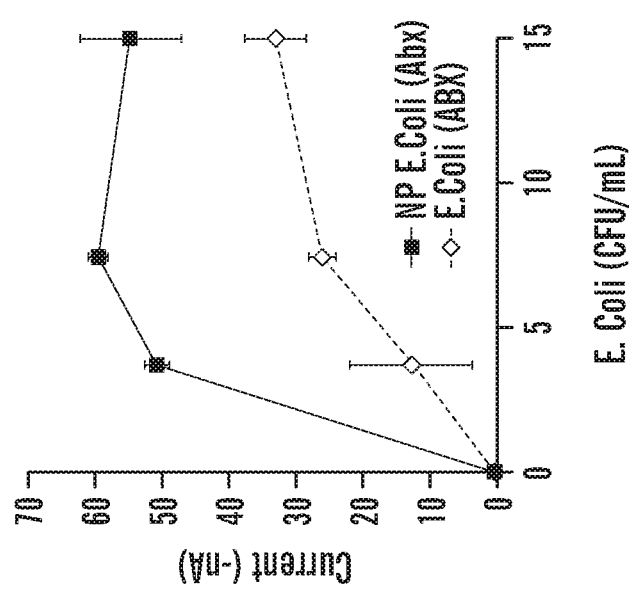
FIGS. 2A and 2B show the effect of sample pretreatment with the addition of nanoparticles on sensor sensitivity.
Figure 2B:
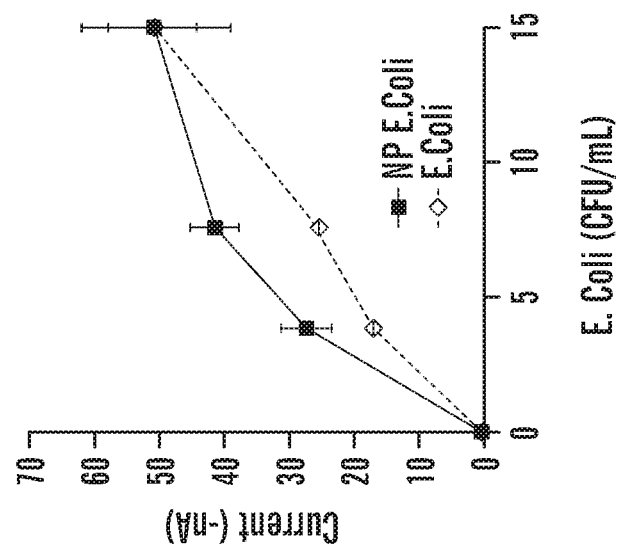
Figure 3A:
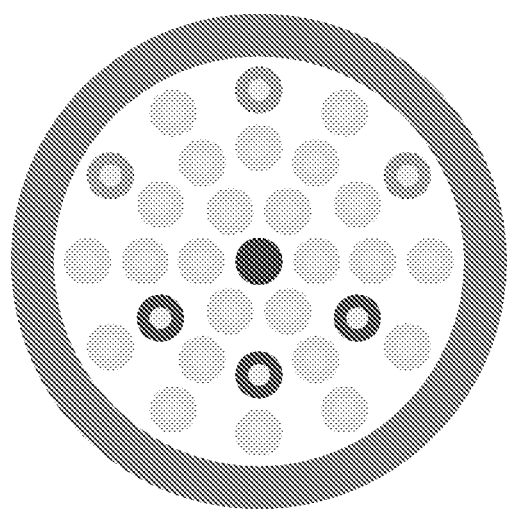
FIG. 3A is a schematic representation of a 32-electrode array arranged in a single 6 mm diameter well, according to one embodiment. (Outer dark grey ring: counter electrode; Green electrodes: antigen specific electrodes; Red and dark green electrodes: positive and negative controls respectively; Light grey central electrode: reference electrode).
Figure 3B:
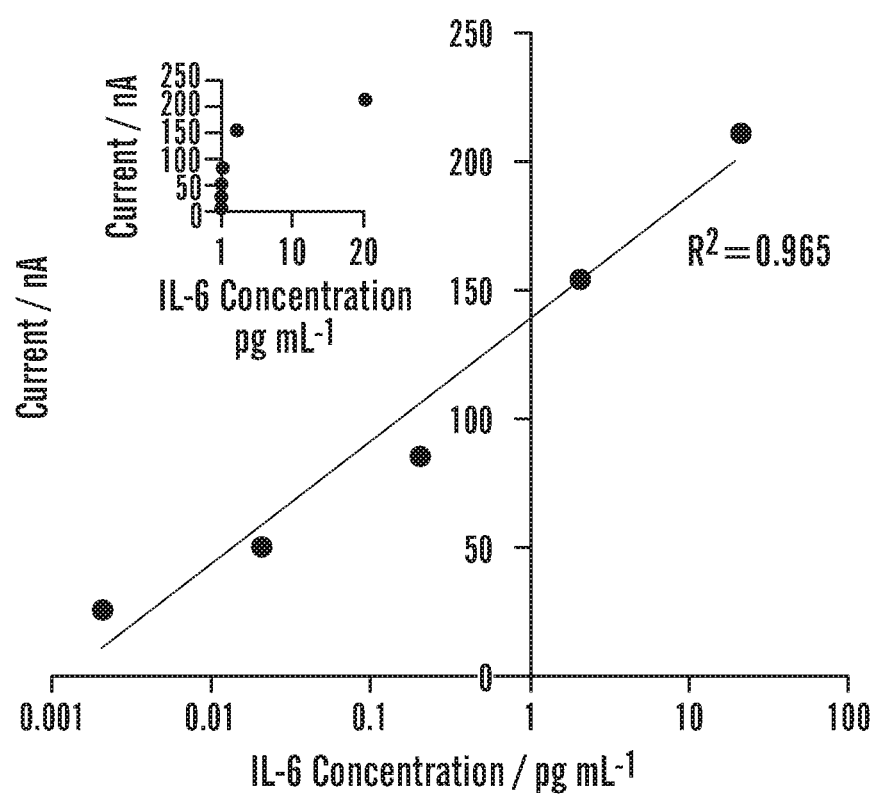
FIG. 3B is a calibration curve obtained for the electrochemical detection of the inflammation protein interleukin-6 (IL-6) in the concentration range of 2 fg/mL-20 pg/mL on a gold electrode. Current measured is proportional to the amount of enzyme bound to the electrode, and therefore to the antigen concentration.

Pre-treating a sample with nanoparticles functionalized with capture probes for specific binding with a target analyte increases sensor sensitivity, as shown in FIGS. 2A-2B. FIG. 2A (left) shows the electrochemical detection of *E. coli* bacteria which were pre-treated with the antibiotic cefepime at a concentration of 100 μg/mL for 4 hours at 37° C. FIG. 2B (right) shows the electrochemical detection of untreated *E. coli*. For both FIGS. 2A and 2B, *E. coli* was obtained as BioBall® (bioMerieux, 15 CFU/mL), and diluted in TBS-Tween $Ca^{2+}$ buffer to 7.5 and 3.75 CFU/mL. The results presented in FIGS. 2A-2B were obtained using a 64-electrode sensor array, each electrode being either modified with FcMBL or a monolayer of thiolated poly(ethylene glycol) used as negative control. Each data point is the average of three sensors. FIGS. 2A-2B demonstrate the sensitivity enhancement resulting from the preconcentration of treated and untreated *E. coli* using FcMBL-coated nanoparticles. Particularly more pronounced at low concentrations, a 4-fold improvement in signal intensity was measured when detecting 3.75 CFU/mL of antibiotic-treated *E. coli*.

Example 4

Figure 5:
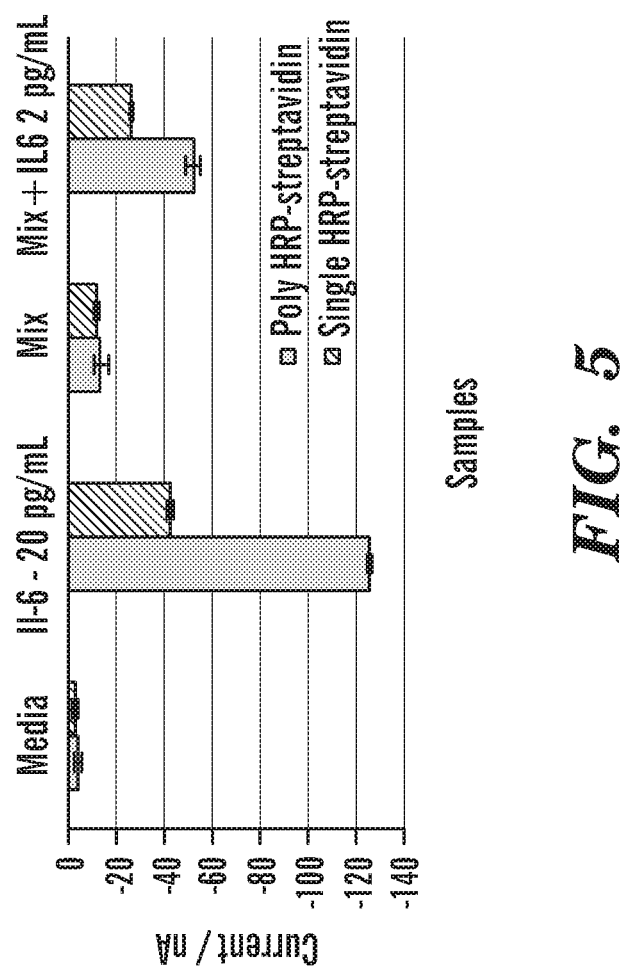
FIG. 5 shows a comparison between labeling with single HRP vs. poly-HRP conjugated streptavidin.

This example illustrates the difference in signal intensity between labeling with single HRP vs. poly-HRP conjugated streptavidin, as shown in FIG. 5. The experiment was carried out in TBS buffer using a flow cell having analyte-specific electrodes functionalized with antibodies raised against interleukin-6 (IL-6). IL-6 bound to the electrodes was labeled with biotinylated anti-IL-6 antibodies, and then labeled with HRP-streptavidin or poly-HRP streptavidin. The flow cells were treated with $H_2O_2$/TMB precipitating composition, then washed with TBS buffer, and current readings were taken from the electrodes. Poly-HRP-streptavidin has 6-8 HRP per streptavidin label. Approximately 3-fold sensitivity enhancement was obtained using poly-HRP streptavidin. IL-6 was detected at 2 pg/mL. Media: control. IL-6: 20 pg/mL. Mix: IL-8: IL-8: 5 ng/mL, GCSF: 125 pg/mL, Rantes: 125 pg/mL, IP10: 12.5 ng/mL., Mix+IL-6: Mix+IL-6 2 pg/mL.

Example 5

Figure 6:
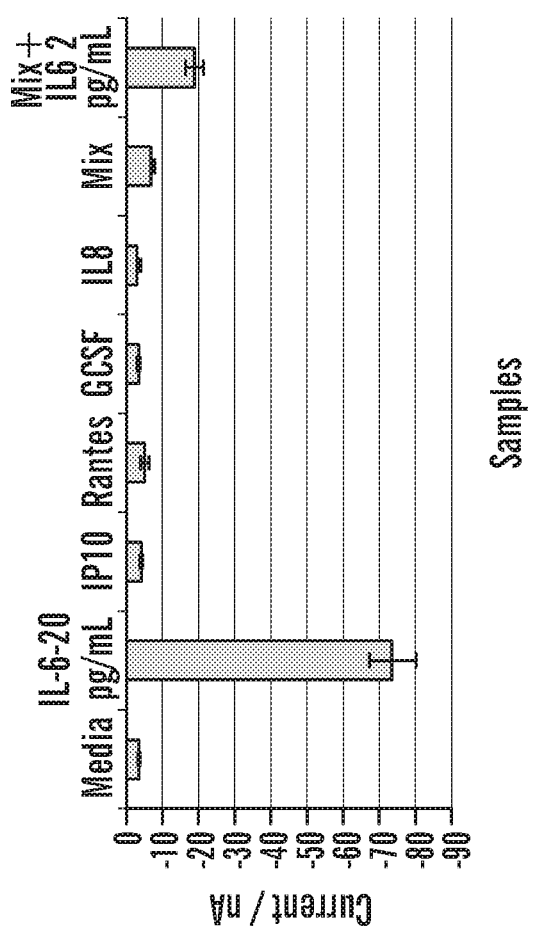
FIG. 6 shows a full cross-reactivity study of anti-IL-6 modified sensors exposed to various individual chemokines and mixtures.

A full cross-reactivity study of anti-IL-6 modified electrochemical sensors exposed to various individual chemokines and mixtures was performed, as shown in FIG. 6. It can be seen that the method and sensor are highly selective for IL-6 detection, and there is a low false-positive reading for other chemokines. Media: control. IL-6: 20 pg/mL. IL-8: 20 ng/mL. G-CSF: 500 pg/mL. Rantes: 500 pg/mL. IP10: 50 ng/mL. Mix: IL-8: 5 ng/mL, GCSF: 125 pg/mL, Rantes: 125 pg/mL, IP10: 12.5 ng/mL. Mix+IL-6: Mix+IL-6: 2 pg/mL.

Example 6

Figure 7:
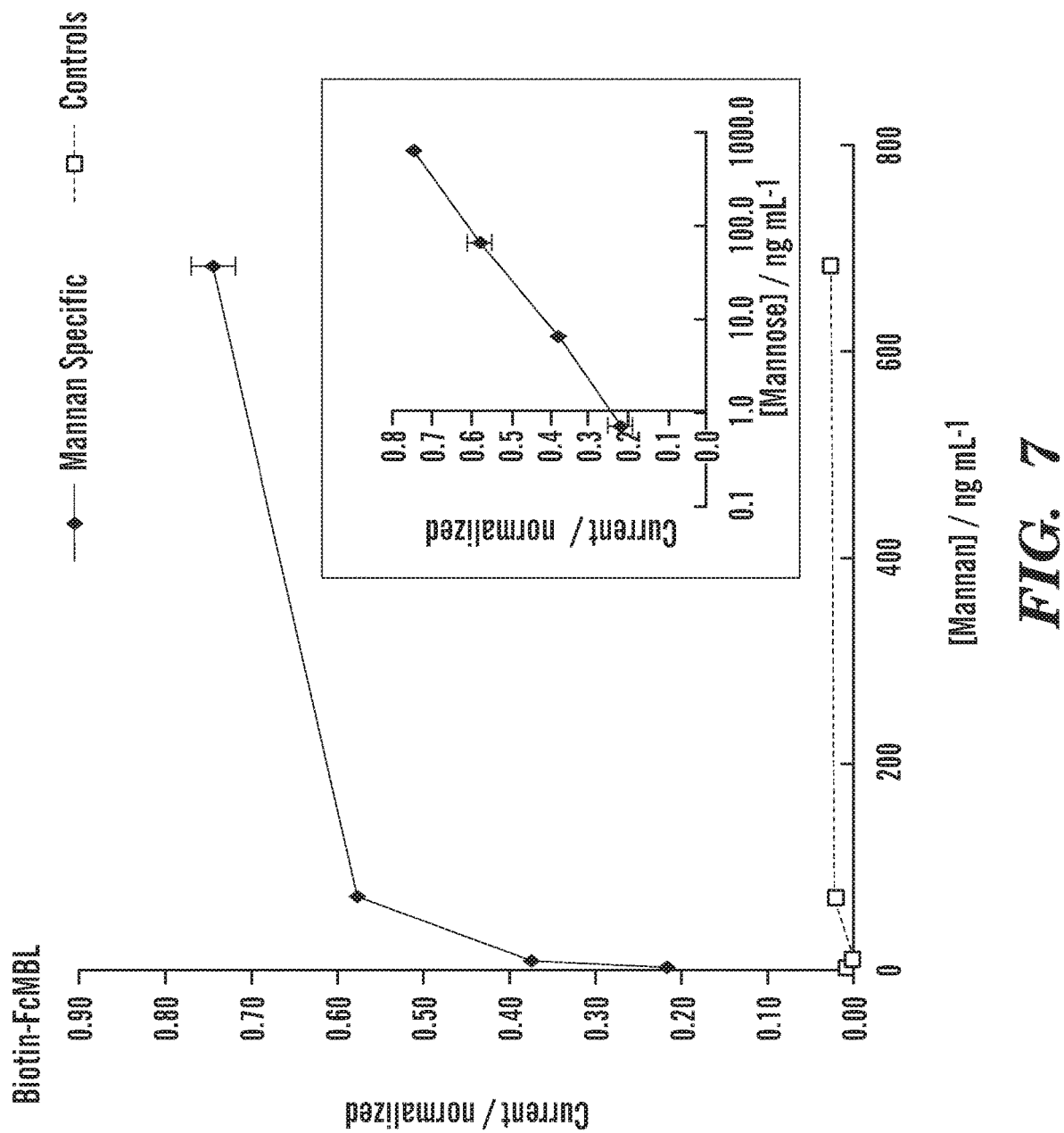
FIG. 7 shows electrochemical detection of mannan in TBS-Tween $Ca^{2+}$ buffer using a biotin-FcMBL labeling approach.

Electrochemical detection of the polysaccharide mannan was performed in TBS-Tween $Ca^{2+}$ buffer using a biotin-FcMBL labeling approach, as shown in FIG. 7. Analyte-specific electrodes functionalized with FcMBL were treated with various concentrations of mannan in TBS buffer. The bound mannan was labeled with biotinylated FcMBL and HRP-conjugated streptavidin. The electrodes were treated with $H_2O_2$/TMB precipitating composition, then washed with TBS buffer, and current readings were taken from the electrodes. This demonstrates the applicability of the sensor platform (also useful for protein detection) for detecting polysaccharides present on bacteria cell walls.

Example 7

Figure 8:
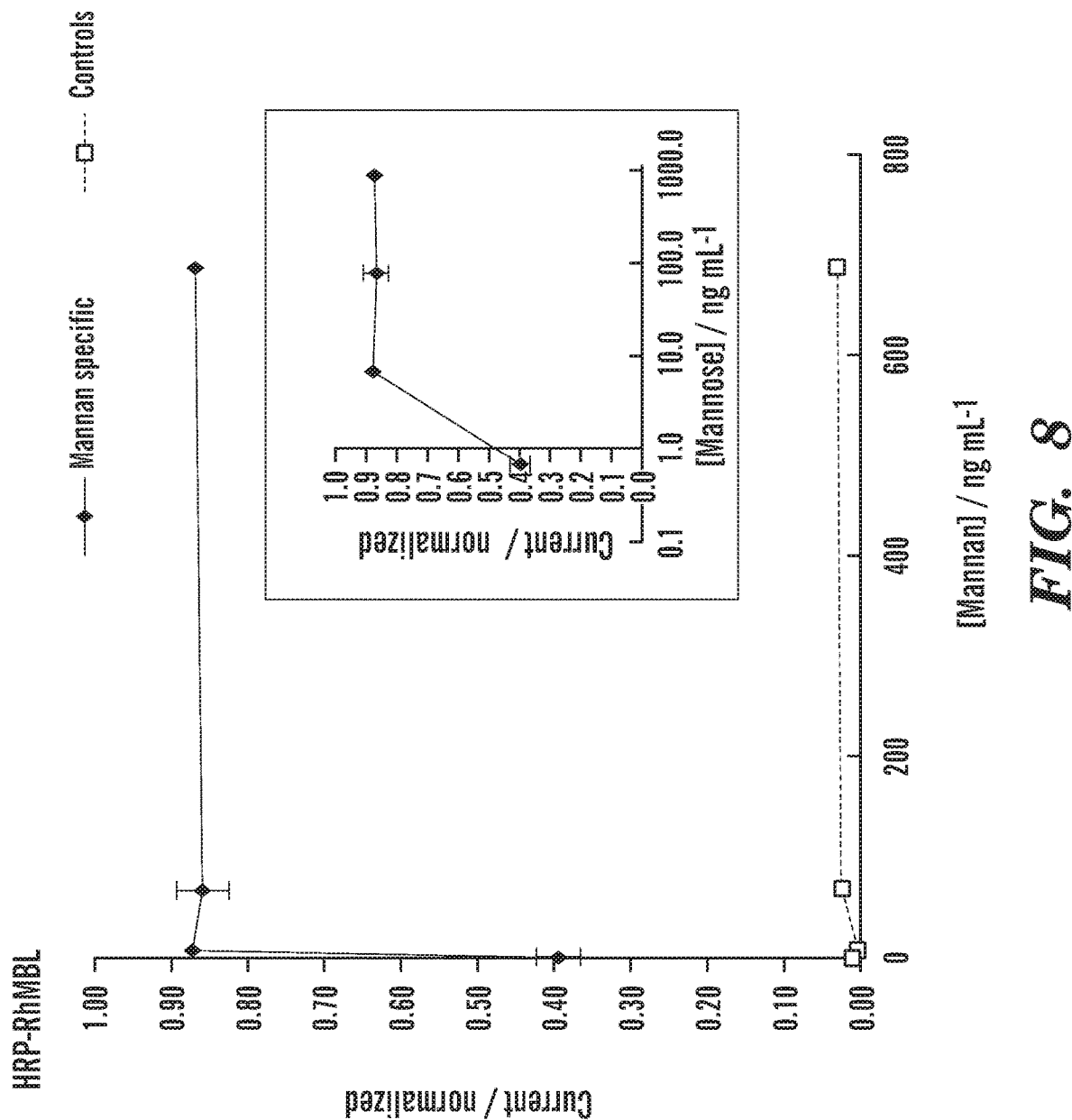
FIG. 8 shows electrochemical detection of mannan in TBS-Tween $Ca^{2+}$ buffer using a HRP-RhMBL labeling approach.
Figure 9B:
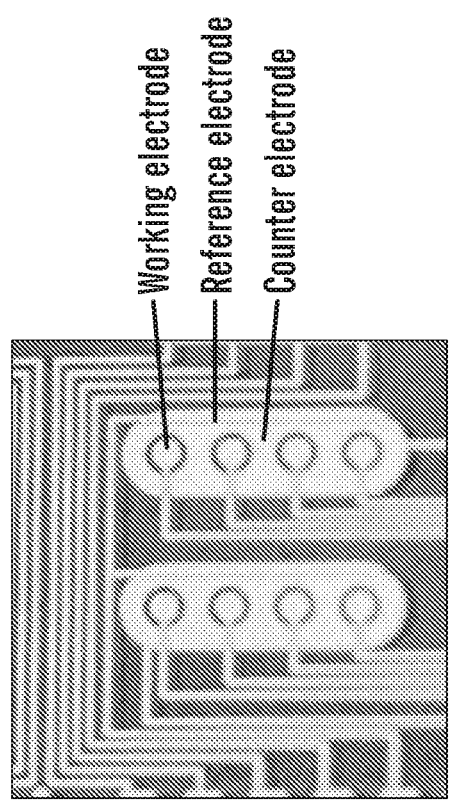
FIG. 9B is an enlarged photograph of the 64-electrode electrochemical sensor chip shown in FIG. 9A and depicts the working electrode, reference electrode and counter electrode.
Figure 9A:
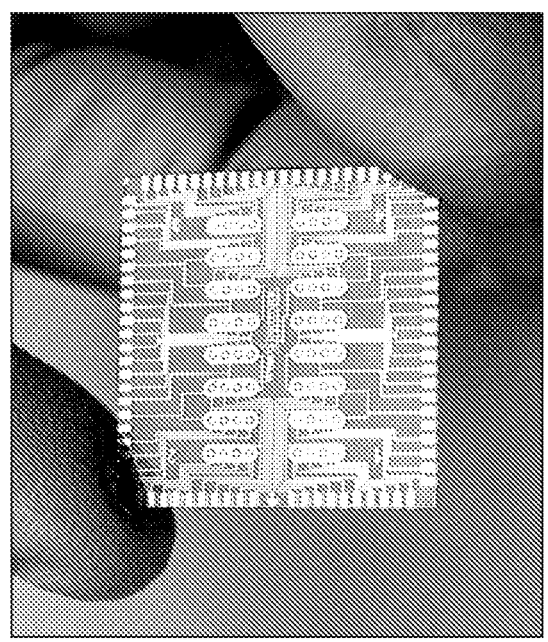
FIG. 9A is a photograph showing a 64-electrode electrochemical sensor chip according to an embodiment of the invention.
Figure 10:
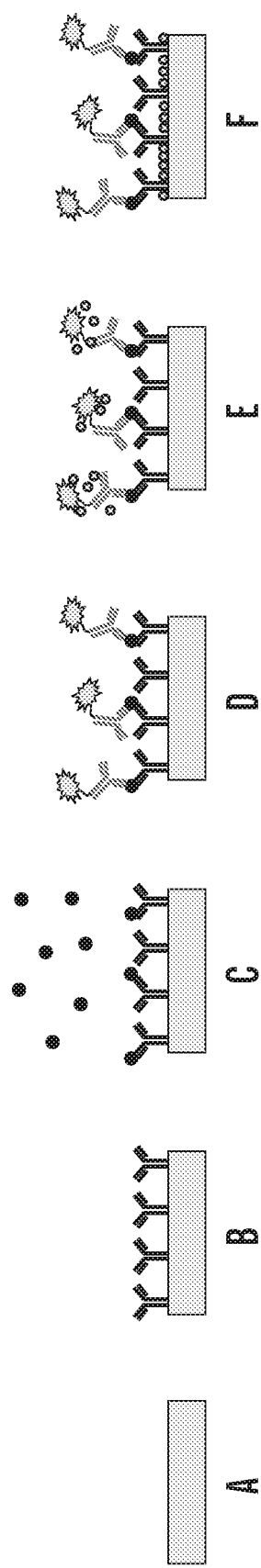
FIG. 10 is a schematic representation of a multiplex assay principle. From left to right, A represents a bare sensor; B represents the sensor modified with antibody; C represents the sensor with target protein bound to antibody when a sample is injected; D represents the sensor when HRP label detection antibody binds to antibody-protein complex; E represents the sensor when the introduced enzyme substrate reacts with tethered enzyme; and F represents the sensor when enzymatic product precipitates out of solution onto the sensor.
Figure 11:
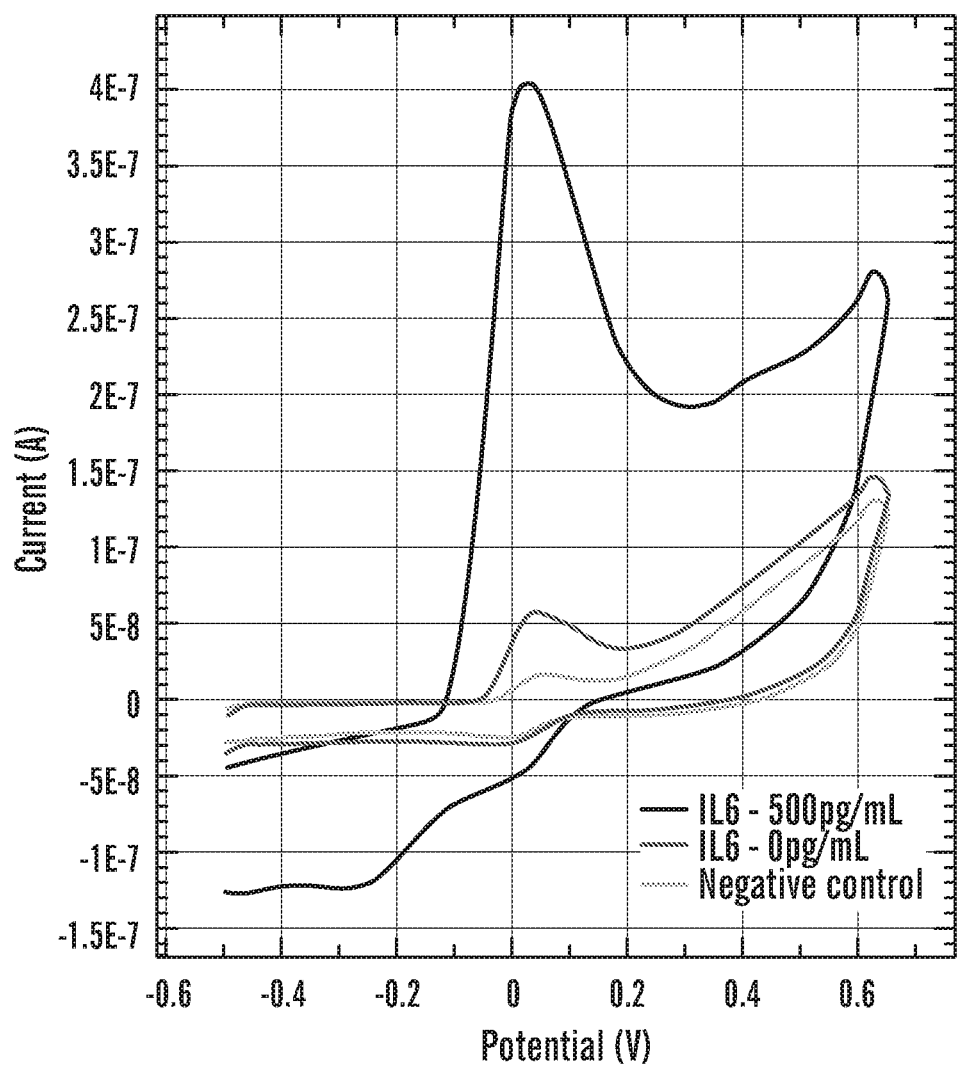
FIG. 11 is a graph showing a typical recorded signal. The potential is scanned from negative to positive, and the current produced due to the presence of the enzymatic product is measured. The signal can be reported as max peak current (I) and/or integrated and reported as charge (C). I or C is proportional to quantity of enzyme bound to the electrode, therefore to the detection antibody, and therefore to the amount of bound protein.

Electrochemical detection of the polysaccharide mannan was performed in TBS-Tween $Ca^{2+}$ buffer using a HRP-RhMBL labeling approach, as shown in FIG. 8. Analyte-specific electrodes functionalized with FcMBL were treated with various concentrations of mannan in TBS buffer. The bound mannan was labeled with HRP conjugated RhMBL. The electrodes were treated with $H_2O_2$/TMB precipitating composition, then washed with TBS buffer, and current readings were taken from the electrodes. This demonstrates the applicability of the sensor platform (also useful for protein detection) for detecting polysaccharides present on bacteria cell walls.

Example 8

Figure 12B:
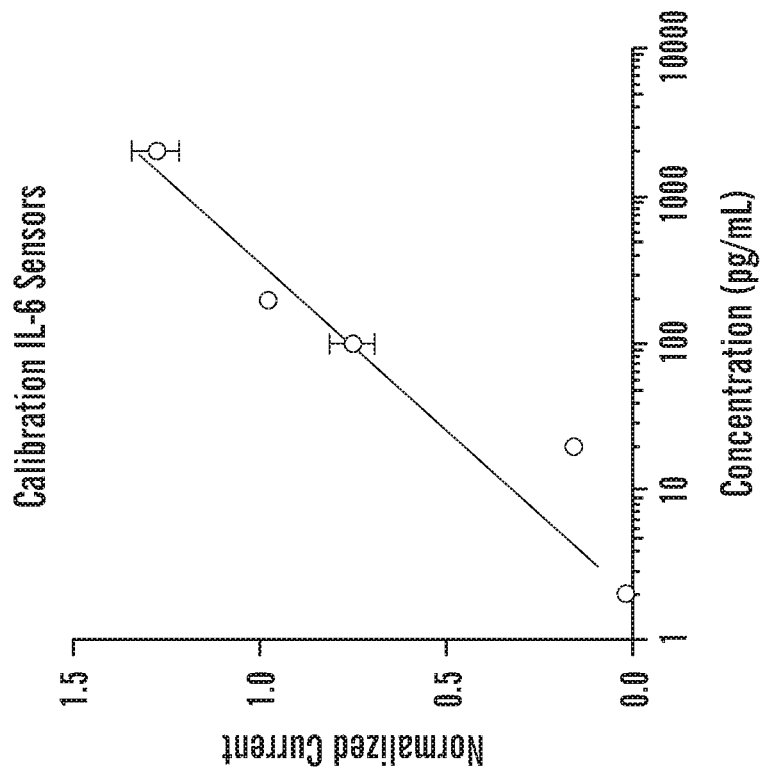
FIGS. 12A and 12B are calibration curves for the simultaneous electrochemical detection of the two inflammatory markers IP-10 and IL-6 in culture media.
Figure 12A:
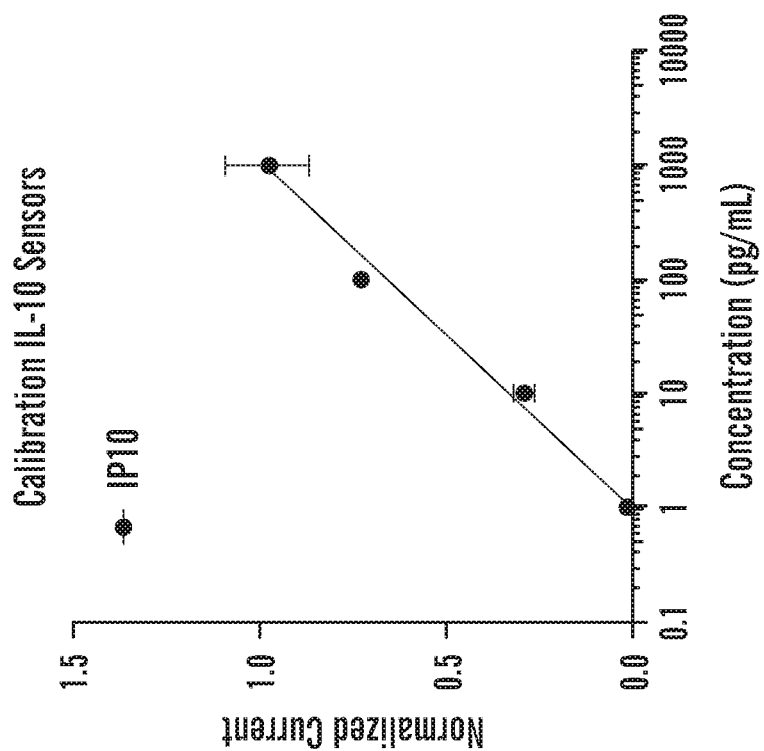

A lung-on-a-chip was infected with rhinovirus. Following infection, the basal and apical compartment of the chip was washed with PBS. The collected samples were analyzed using multiplex electrochemical assay. Calibration curves for the simultaneous electrochemical detection of the two inflammatory markers IP-10 and IL-6 in culture media are shown in FIGS. 12A and 12B. Standards containing both IP-10 and IL-6 at known concentration were prepared in culture media.

Figure 13B:
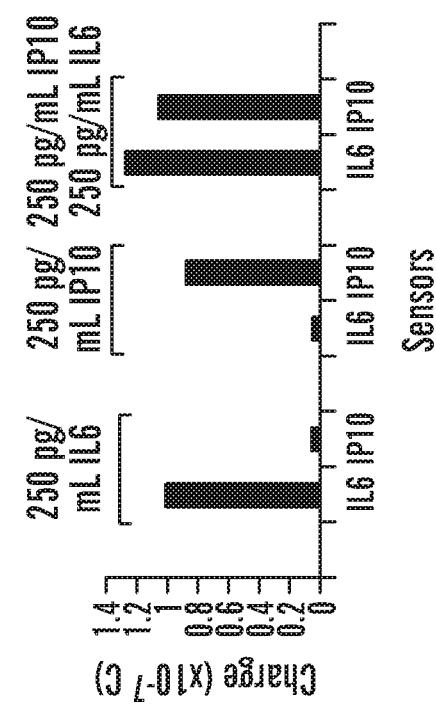
FIGS. 13A and 13B are bar graphs showing reproducibility across single array 5.5%, 100 pg/mL, n=18 for protein sensors and n=6 for controls (FIG. 13A), and cross reactivity and simultaneous protein detection (FIG. 13B).
Figure 13A:
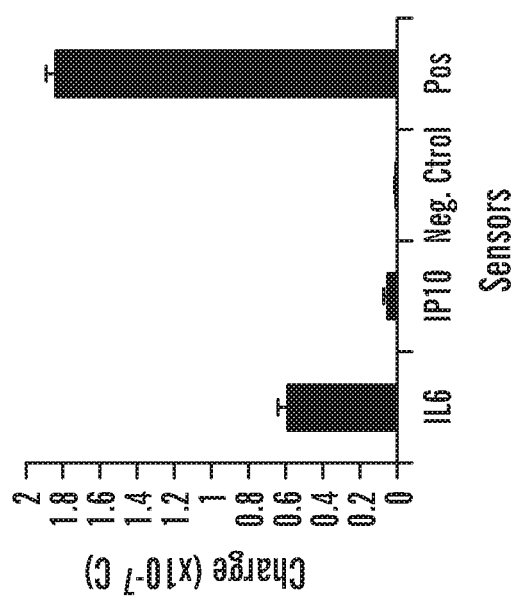

Evaluation of cross-reactivity and reproducibility data is shown in FIGS. 13A and 13B. One flow cell comprising sensors for IL-6 and sensors for IP-10, as well as negative control (i.e. No antibody attached) and positive sensors (i.e. Biotin-modified) was filled with a sample containing IL-6 at a concentration of 100 pg/mL. The assay was completed by adding the biotin-labeled detection antibody, followed by streptavidin-HRP and finally the precipitating TMB reagent. The IL-6 specific sensors clearly indicated the presence of IL-6 in the sample while the signals measured at the IP-10 specific and the negative control remained very low. The positive control sensor signal was very high as expected, as it should bind large amount of streptavidin-HRP. Sensors sequentially modified with IL-6 or IP10 antibodies in a single flow cell were exposed to either 250 pg/mL IL-6, or 250 mg/mL IP-10 or 250 pg/mL of both protein. The responses measured indicate that no or little cross-reactivity occurs at the surface of the sensors.

Figure 14A:
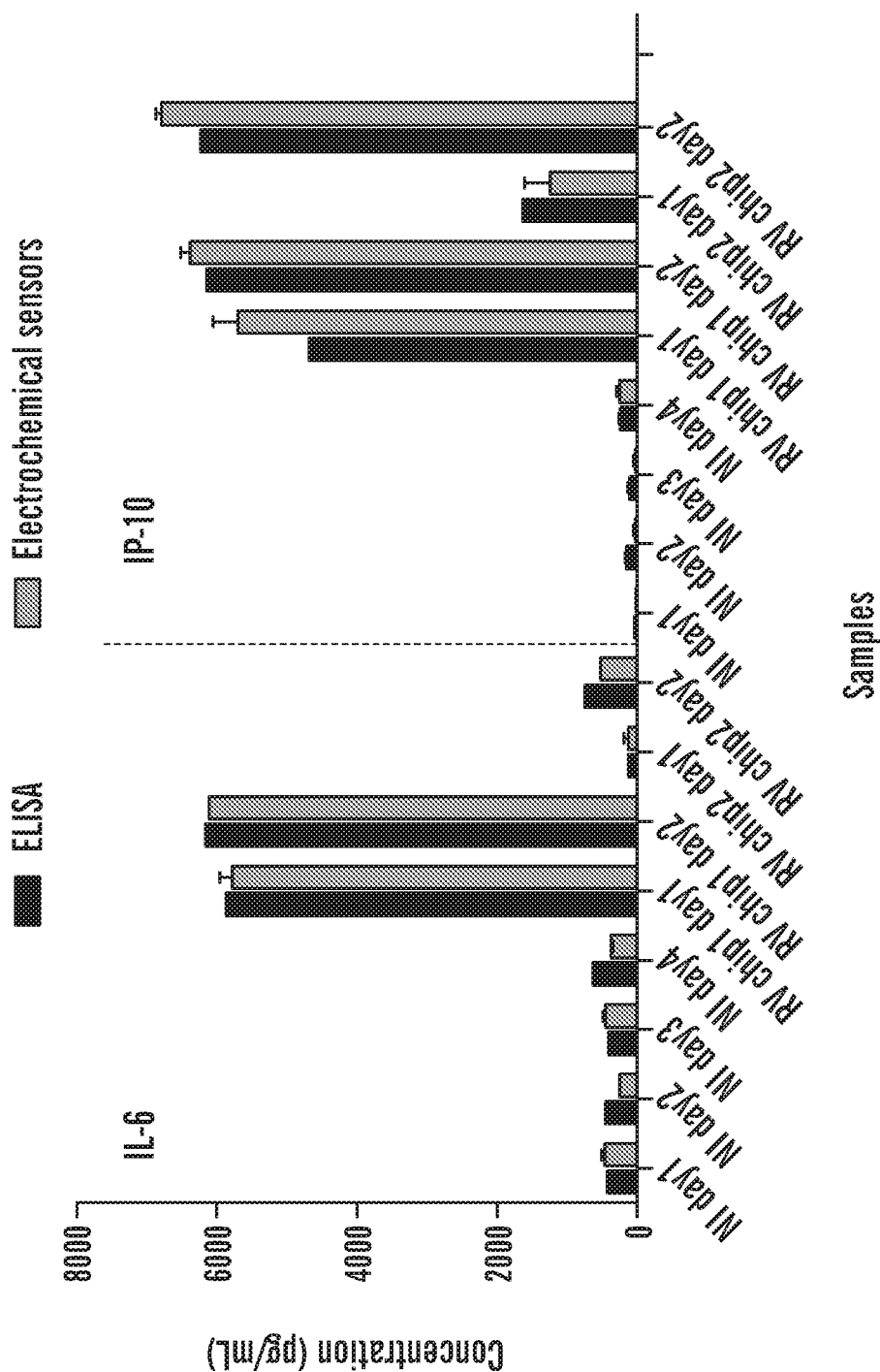
FIG. 14A is a bargraph showing side-to-side comparison of the calculated concentration measured using traditional ELISA kits (black bars) necessitating 1 kit for each protein and simultaneously measuring on the electrochemical platform (light grey bars). (NI: non infected chip; RV: Rhinovirus infected chip).
Figure 14B:
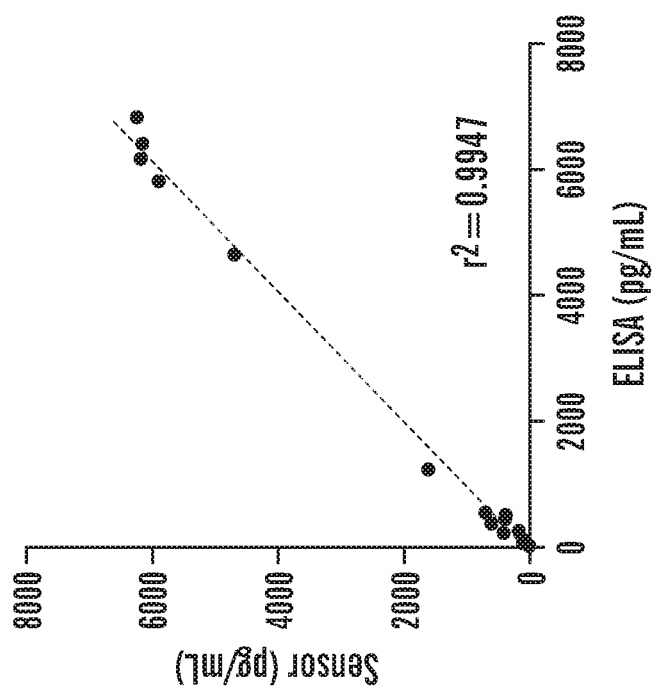
FIG. 14B shows a correlation graph for all concentration presented in FIG. 14A. The correlation was excellent with an $r^2$ value of 0.9947.

Correlation of the electrochemical results and ELISA results is presented in FIGS. 14A and 14B. Side-to-side comparison of the calculated concentration measured using traditional ELISA kits (black bars, 1 kit for each protein) and simultaneously measured on the electrochemical platform (light grey bars, NI: non infected chip; RV: Rhinovirus infected chip) shows that the correlation was excellent with an $r^2$ value of 0.9947. This experiment demonstrates multiplexed electrochemical detection of several proteins in a single sample exiting a lung-on-a-chip infected with rhinovirus.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

What is claimed is:

1. A method for detecting a target analyte in a sample, comprising:
   (a) introducing a sample comprising a target analyte into an electrochemical sensor comprising a fluid-contact surface and an analyte-specific electrode immobilized on at least a portion of the fluid-contact surface, wherein the analyte-specific electrode is functionalized with a first capture probe for specific binding with the target analyte;
   (b) allowing the target analyte to bind with the capture probe on the analyte-specific electrode, thereby forming a complex comprising the target analyte and the capture probe on a surface of the analyte-specific electrode;
   (c) labeling the complex with a label probe, wherein the label probe binds specifically with the target analyte and the label probe is conjugated with at least one reporter enzyme;
   (d) introducing simultaneously a reporter enzyme substrate, an electroactive mediator and a precipitating agent, forming an electroactive mediator precipitating composition, into the electrochemical sensor, wherein a reaction of the electroactive mediator precipitating composition with the at least one reporter enzyme conjugated with the label probe forms an electroactive precipitate locally adsorbed at the surface of the analyte-specific electrode;
   (e) applying a voltage to the electrochemical sensor, wherein the voltage corresponds to the standard redox potential of the electroactive precipitate; and
   (f) measuring a current generated from the analyte-specific electrode of the electrochemical sensor to detect the target analyte;
   wherein the target analyte is not a nucleic acid.

2. The method of claim 1, further comprising prior to step (a):
   i. mixing a sample comprising the target analyte with a plurality of nanoparticles, wherein at least one nanoparticle of said plurality of nanoparticles is functionalized with a second capture probe for specific binding with the target analyte; and
   ii. allowing the target analyte to bind with the capture probe on said at least one nanoparticle.

3. The method of claim 2, wherein the nanoparticle is a magnetic nanoparticle, a gold nanoparticle, a silver nanoparticle, a semiconductor nanoparticle, or a polymeric nanoparticle.

4. The method of claim 2, wherein at least two of the nanoparticles are functionalized with capture probes for specific binding with at least two different target analytes.

5. The method of claim 2, wherein the complex in step (b) comprises the at least one nanoparticle.

6. The method of claim 1, wherein the electrochemical sensor comprises a plurality of analyte-specific electrodes immobilized on at least a portion of the fluid-contact surface, wherein each analyte-specific electrode in said plurality of analyte-specific electrodes is functionalized with a capture probe for specific binding with a specific target analyte.

7. The method of claim 6, wherein at least two of the analyte-specific electrodes are adapted to detect different target analytes.

8. The method of claim 1, further comprising, prior to the step of applying the voltage to the electrochemical sensor, washing the electrochemical sensor to remove any electroactive mediator precipitating composition or electroactive precipitate that is not adsorbed at the analyte-specific electrode surface.

9. The method of claim 1, wherein the electrochemical sensor comprises one or more microfluidic flow cells.

10. The method of claim 1, wherein the electrochemical sensor comprises one or more open wells.

11. The method of claim 1, wherein the analyte-specific electrode is a planar or 3- dimensional electrode.

12. The method of claim 1, wherein the fluid-contact surface further comprises a counter electrode and a reference electrode immobilized thereon.

13. The method of claim 1, wherein the fluid-contact surface further comprises a positive control electrode and/or a negative control electrode immobilized thereon.

14. The method of claim 1, wherein the voltage applied to the electrochemical sensor corresponds to an electrochemical reduction or oxidation potential of the electroactive mediator in a fully or partially oxidized state.

15. The method of claim 1, wherein the generated current corresponds to a reduction or oxidation current derived from reduction of the fully or partially oxidized electroactive mediator.

16. The method of claim 1, wherein the fluid-contact surface is a non-electrically conductive surface.

17. The method of claim 1, wherein the capture probe and label probe comprise a carbohydrate binding protein, wherein the carbohydrate binding protein comprises a carbohydrate recognition domain of mannan-binding lectin (MBL).

18. The method of claim 1, wherein the electroactive mediator is selected from the group consisting of 3,3',5,5'-tetramethylbenzidine (TMB), o-phenylenediamine dihydrochloride (OPD), 2,2'-Azinobis [3-ethylbenzothiazoline-6-sulfonic acid] (ABTS), p-Nitrophenyl Phosphate (PNPP), 3,3'-diaminobenzidine (DAB), 4-chloro-1-naphthol (4-CN), 5-bromo-4-chloro-3-indolyl-phosphate (BCIP), nitro blue tetrazolium (NBT), methylene blue, hydroquinone, ferrocene derivatives, and any combination thereof.

* * * * *